(12) United States Patent
Pons

(10) Patent No.: US 12,364,503 B2
(45) Date of Patent: Jul. 22, 2025

(54) HELICAL SEPARATOR AND METHODS OF OPERATING THE SAME

(71) Applicant: Penumbra, Inc., Alameda, CA (US)

(72) Inventor: Stephen Joseph Pons, Alameda, CA (US)

(73) Assignee: Penumbra, Inc., Alameda, CA (US)

( * ) Notice: Subject to any disclaimer, the term of this patent is extended or adjusted under 35 U.S.C. 154(b) by 0 days.

(21) Appl. No.: 18/492,674

(22) Filed: Oct. 23, 2023

(65) Prior Publication Data
US 2024/0115290 A1 Apr. 11, 2024

Related U.S. Application Data

(63) Continuation of application No. 17/463,939, filed on Sep. 1, 2021, now Pat. No. 11,793,542.

(51) Int. Cl.
*A61B 17/3207* (2006.01)

(52) U.S. Cl.
CPC ........... *A61B 17/320758* (2013.01); *A61B 2017/320733* (2013.01); *A61B 2017/320775* (2013.01)

(58) Field of Classification Search
CPC ........... A61B 17/22; A61B 17/3498; A61B 17/320758; A61B 17/320725; A61B 17/32075; A61B 17/320783; A61B 2017/320733; A61B 2017/00561; A61B 2017/00022; A61B 2017/320775; A61B 2017/320791; A61B 2090/064; A61B 90/06

See application file for complete search history.

(56) References Cited

U.S. PATENT DOCUMENTS

| | | | |
|---|---|---|---|
| 5,195,954 A * | 3/1993 | Schnepp-Pesch | A61B 17/320758 606/127 |
| 7,563,242 B2 * | 7/2009 | Yaguchi | A61F 9/00745 604/43 |
| 2002/0058956 A1 * | 5/2002 | Honeycutt | A61B 17/320758 606/159 |
| 2005/0149096 A1 * | 7/2005 | Hilal | A61M 25/0068 606/191 |
| 2008/0097499 A1 * | 4/2008 | Nash | A61B 17/32037 606/159 |
| 2017/0239447 A1 * | 8/2017 | Yang | A61M 25/10 |

* cited by examiner

*Primary Examiner* — Tuan V Nguyen
(74) *Attorney, Agent, or Firm* — Baker Botts L.L.P.

(57) ABSTRACT

In one embodiment, an aspiration thrombectomy system includes an aspiration catheter having a proximal end, a distal end, and a lumen to accommodate fluid, a first valve capable of removing fluids from the system to alter a level of pressure in the system in a first manner, a second valve capable of providing fluids into the system to alter the level of pressure in the system in a second manner, and a cutting instrument at the distal end of the aspiration catheter having a spiral body connected to a rounded element having a scooped-out portion for engaging a target occlusive material, the cutting instrument being capable of axial and rotational motion, and the system being capable of cutting and removing the occlusive material based on the motions of the cutting instrument and one or more of the first manner and the second manner of altering the level of pressure.

20 Claims, 19 Drawing Sheets

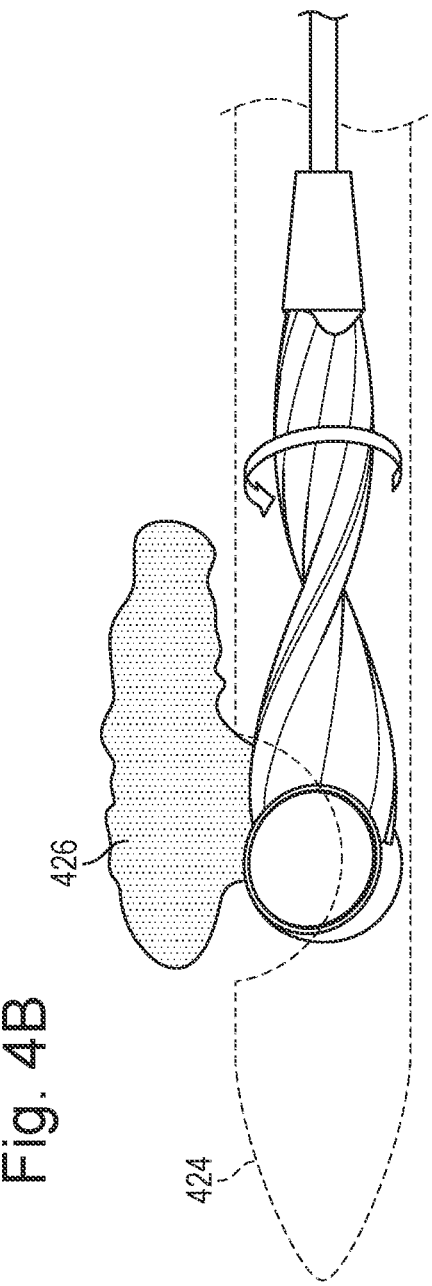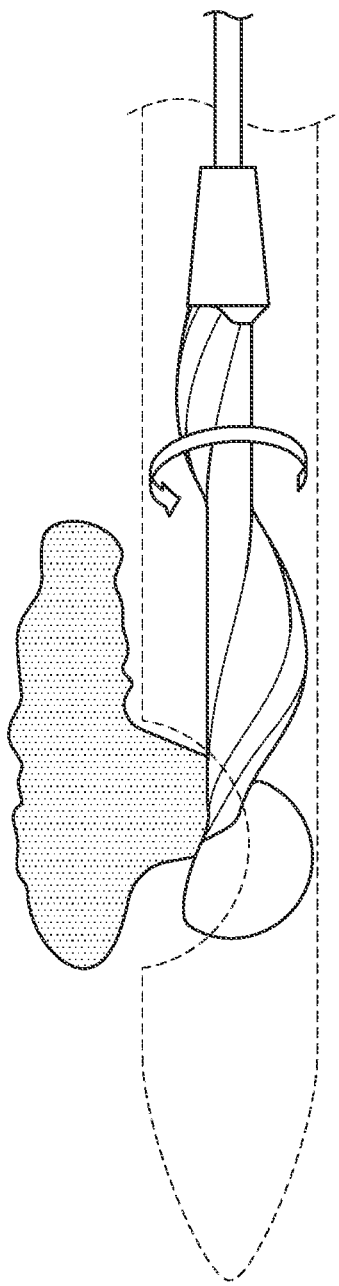
Fig. 4B
Fig. 4C

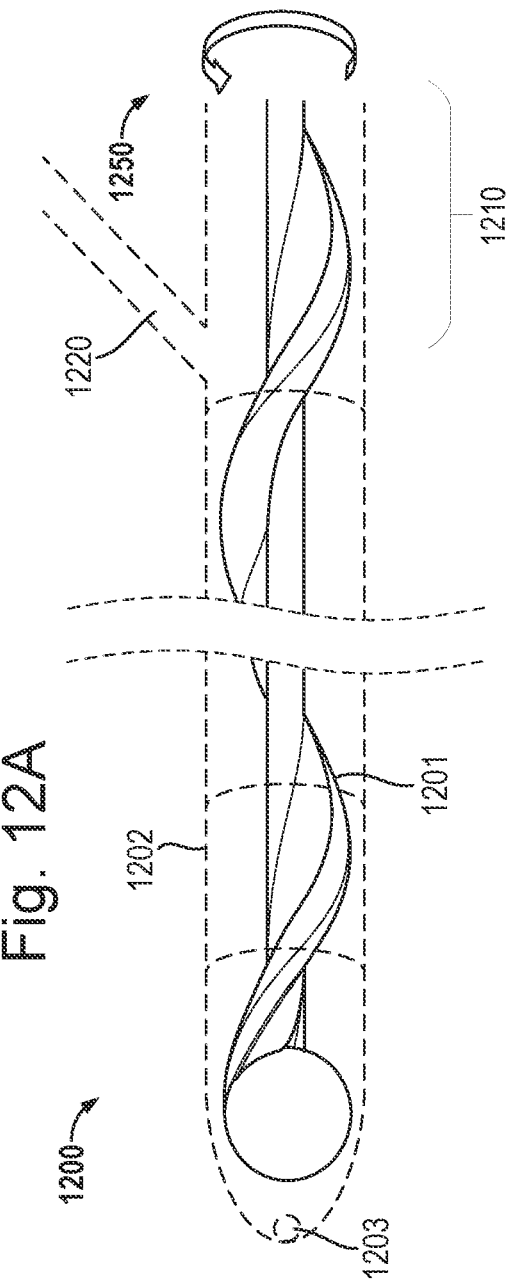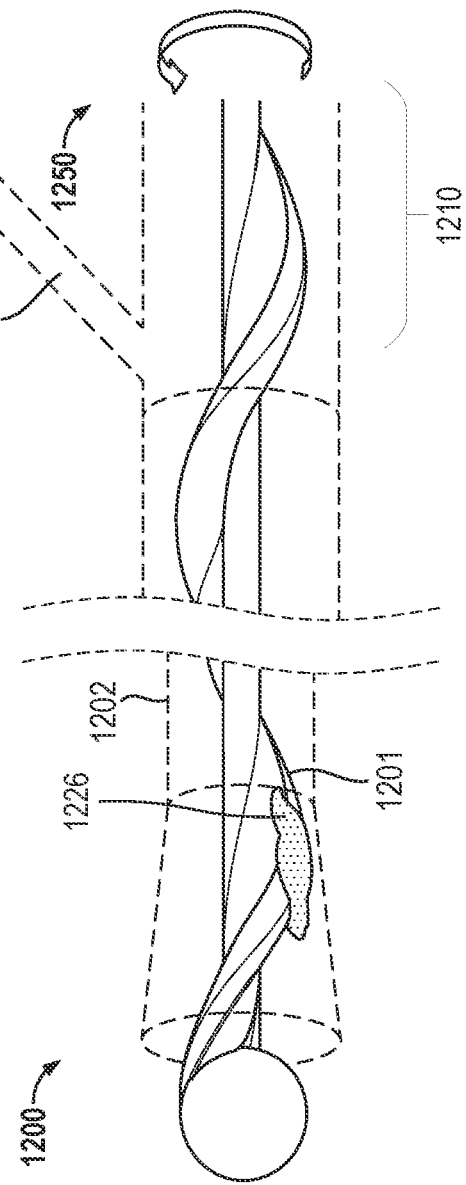

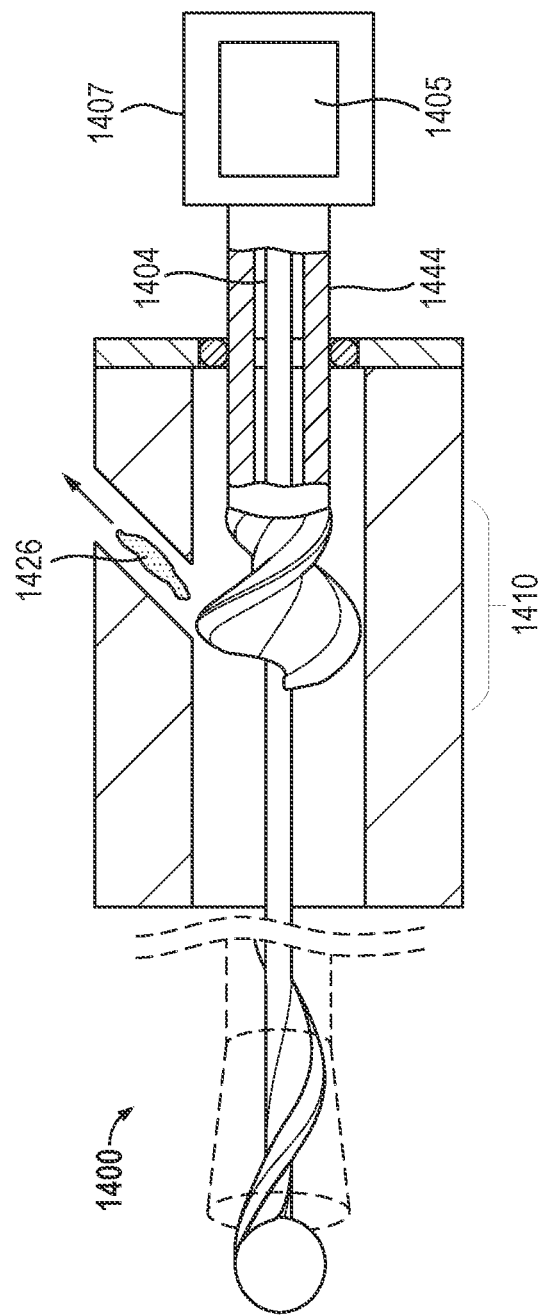

HELICAL SEPARATOR AND METHODS OF OPERATING THE SAME

PRIORITY

This application is a continuation under 35 U.S.C. § 120 of U.S. patent application Ser. No. 17/463,939, filed 1 Sep. 2021, issued as U.S. Pat. No. 11,793,542, which is incorporated herein by reference.

BACKGROUND

The present application relates generally to medical devices and methods. More particularly, the present application relates to medical devices and methods for cutting, collecting, and removing occlusive material from blood vessels and other body lumens.

SUMMARY OF PARTICULAR EMBODIMENTS

Many factors can cause an undesirable buildup of occlusive material in the vascular system. For example, thrombosis (the formation of a blood clot) and atherosclerosis (buildup of fats, cholesterol and other substances on a wall of a blood vessel) are common conditions that can result in a buildup of material that at least partially blocks a blood vessel. These deposits restrict blood flow and pose a risk of fragmenting into the blood stream. If this fragmented material travels to the heart, brain, or lungs, the event can be fatal. An example of one such disease state is Deep Venous Thrombosis (DVT), where blood clots form in the deep (non-superficial) veins of the body, typically within the legs. DVT is commonly characterized by the build-up of large volumes of tough, chronic clot which impedes venous flow. As such, there exists a need for an effective treatment that not only addresses the complication but also prevents the proliferation and reoccurrence of further, related complications.

The removal of occlusive material from blood vessels and other body lumens has commonly been approached through treatments based on drug administration, filter implants, and catheter-based removal. Anticoagulant drugs, such as Heparin, are the most commonly prescribed treatments, e.g., for DVT. The administration of anticoagulants helps prevent a clot from growing and relies on the body's lysing processes to eliminate the clot. This process is expensive, slow acting, not effective against large or complete occlusions, and risks residual clot entering the blood stream to cause venous damage elsewhere.

Thrombus filter implantation is used as a preventative measure for those at risk of developing clots. These filters are surgically implanted, typically into the inferior vena cava. Filters function to capture clot and then allow the body's lysing processes to eliminate the clot. Although the use of these filters can greatly reduce the likelihood of clot fragments traveling to the heart or lungs, they often require the use of anticoagulant drugs in concert and therefore entail all the complications described above. Furthermore, poor rates of physician follow-up and patient compliance result in a low percentage of filters ever being retrieved.

Catheter-based interventions present an alternative treatment method. Catheters or catheter-based devices are percutaneously introduced into blood vessels and are maneuvered into direct contact with a target substance. For newly formed thrombus or unadhered and small plaque, the substance may be removed through a catheter via aspiration, mechanical capture, or other means. This approach has the benefit of quickly removing the target substances and the benefit of leaving behind little residual material, which could otherwise lead to reoccurrence or proliferation of related diseases. However, the limitations on the type and volume of occlusive material which can be successfully removed make it a non-viable approach to many disease states, such as a subset of DVT which can involve large, tough thrombus burdens.

Some catheter-based devices include rotating blades, high pressure water jets, laser ablation, or other aggressive means of breaking up the target material. Such methods are common in atherectomy-specific tools where the occlusion is formed by well-adhered plaque. Many such devices can suffer from at least one of two shortcomings. Firstly, the methods of removing targeted substances once the substances are fragmented can be either ineffective or non-existent. For example, some devices have small lumens that are prone to clogging or inefficient pressure gradients that fail to pull dislodged clot or plaque into the system. If not removed, dislodged clot or plaque is released into downstream blood vessels and poses a risk for further complications. Secondly, devices that use blades to fragment a tough clot or plaque might lead to damage of the wall of a blood vessel.

For the reasons discussed above, there has existed an unmet need for methods and apparatus that remove a wide range of occlusive materials, including at least clot, thrombus, and atheroma, quickly and safely without damaging the surrounding blood vessels.

Accordingly, in accordance with an implementation of the subject matter disclosed herein, a catheter, e.g., a thrombectomy catheter, for use in a subject's vasculature includes a rotatable and/or axially movable cutting instrument. The cutting instrument may be a spiral-shaped, e.g., helical-shaped, cutting instrument. The cutting instrument includes a rounded, e.g., spherical, substantially spherical or partially spherical, element at its distal end. The rounded element is connected to a body having a twisted shape, e.g., a spiral and/or helical shape. The cutting instrument is disposed in a lumen of the catheter and is configured for axial and/or rotational motion within the lumen between a proximal-most position and a distal-most position. In some examples, the body includes at least one edge configured to promote the movement of a target substance towards a proximal end of the lumen upon contact, or close proximity to, the target substrate.

In accordance with one example, the cutting instrument is configured to distally advance outside of the lumen of the catheter, and, optionally, proximally retract inside of the lumen of the catheter. In still another example, the body of the cutting element includes at least two edges positioned on opposite sides, e.g., on radially opposite sides of the body of the cutting element. In an implementation of such an example, a first edge of the two edges of the body is blunt, e.g., substantially blunt, and a second edge of the two edges of the body is sharp, e.g., substantially sharp. The second edge may be configured to promote cutting of the target substance. In the context of the present disclosure, the term "blunt", when describing an edge, is understood to mean not sharpened. In the context of the present disclosure, the term "sharp", when describing an edge, is understood to mean sharpened, e.g., to a knife edge or razor edge to enable it to cut or pierce something. To add context to these terms, a blunt edge may be a rounded edge, e.g., an edge having a radius of approximately 1/32 of an inch, and a sharp edge may be chamfered edge, e.g., an edge having approximately a 30-degree knife edge chamfer. In some examples, the terms "sharp" and "blunt" may be used relatively. For example, the first edge of the body may be an edge that is sharper than the second edge. Similarly, the second edge of the body may be an edge that is blunter than the first edge. In some examples, the first and second edges of the two edges of the body are configured in the same, or similar, manner. For example, the first and second edges may each be blunt. Alternatively, the first and second edges may each be sharp. In some examples, either the first edge or second edge of the body may be configured to sever a portion of the target substance by urging a portion of the target substrate against an edge of an opening in the lumen of the catheter.

In one example, the catheter further includes at least one motor coupled with the cutting instrument, wherein the at least one motor is configured to impart rotational motion and/or axial motion, e.g., reciprocal axial motion, to the cutting instrument. In another example, the body includes a shaft, e.g., a cylindrical shaft, having a spiral shape surrounding the shaft. In an example, the body includes a central smooth surface configured to urge a cut portion of the target substance from a distal end of the body towards a proximal end of the body.

In an example, the rounded element includes at least one scooped-out portion, e.g., at, or near to, where the rounded element connects to the body. The at least one scooped-out portion may include an edge configured to promote cutting of the target substance. The at least one scooped-out portion includes a blunt, or substantially blunt, leading edge and a sharp, or substantially sharp, trailing edge configured to promote cutting of the target substance, where the leading edge is configured to engage the target substance and pull the target substance into the at least one scooped-out portion, during use.

The rounded element may include at least two scooped-out portions on opposites sides of the body of the cutting element. In some examples, each of the scooped-out portion include an edge configured to promote cutting of the target substance. In some examples, each of the scooped-out portions include a leading blunt, or substantially blunt, edge and a trailing sharp, or substantially sharpened, edge configured to promote cutting of the target substance. In some examples, each of the leading edges is configured to engage the target substance and pull the target substance into the corresponding scooped-out portion, during use.

The rounded element may include a wire element, e.g., a loop of wire, a coiled loop of wire, and/or a wire hooked element. The wire element may extend from a first edge of the body to a second edge of the body.

In accordance with an implementation of the subject matter disclosed herein, there is provided a method for removal a target substance from a body passageway using an instrument, such as any appropriate instrument described herein. The instrument comprises a catheter comprising a lumen having a distal edge, and a rotatable body comprising first and second edges configured to promote removal of the target substance from the body passageway upon contact with the target substance. The method comprises urging, e.g., pulling, the target substance into the lumen using the first edge of the body to cause a portion of the target substance to engage the distal end of the catheter. The method comprises separating the portion of the target substance from the body passageway using a cutting, e.g., shearing, action implemented by cooperation between the second edge of the body the distal end of the catheter. For example, where the second edge comprises a curved, e.g., spiraled edge, a shearing action may be implemented as a result of the rotation of the second edge relative to the distal edge of the catheter. The action of urging the target substances into the lumen using the first edge and separating the portion of the target substance from the body passageway using a cutting action may occur in parallel.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which:

FIGS. 4B-4E show a side, transparent, detail view of the helical cutting instrument of FIG. 4A in operation, in accordance with some examples of the disclosure;

FIGS. 12A-12C show a side detail view of another implementation of the helical cutting instrument with a macerating portion, in accordance with some examples of the disclosure;

FIG. 14 shows a cross-section of a macerating portion of another implementation of the catheter system, in accordance with some examples of the disclosure.

DESCRIPTION OF EXAMPLE EMBODIMENTS

Figure 1:
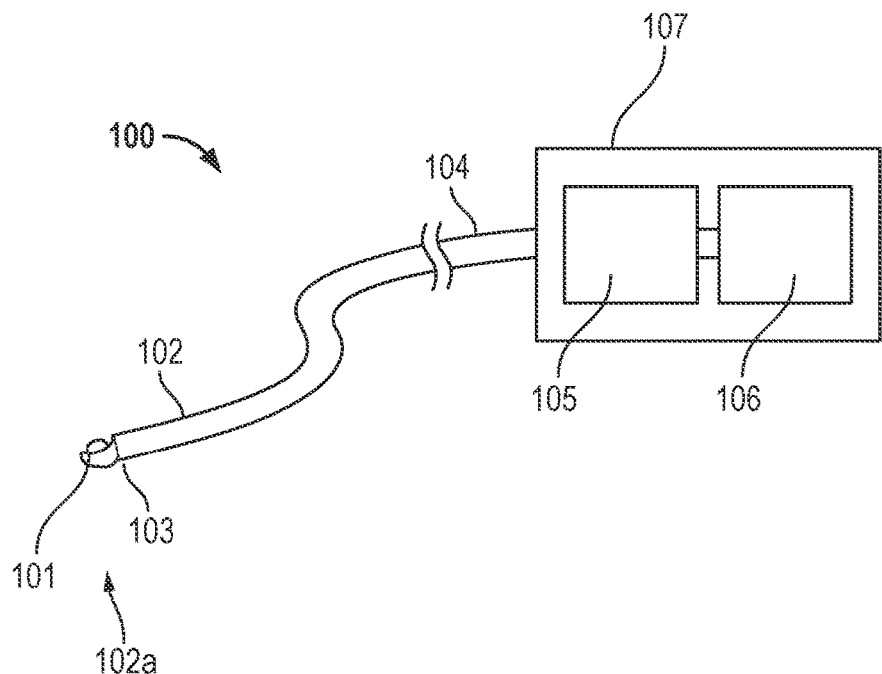
FIG. 1 shows a perspective view of a thrombectomy catheter system, in accordance with some examples of the disclosure.

Devices and methods of operating the same are described herein for removal of one or more target substances from a body passageway.

Directional or positional terminology, such as "top," "bottom," "front," "back," "leading," "trailing," etc., is used with reference to the orientation of the figure(s) being described. Because components of examples of the present invention can be positioned in several different orientations, this terminology is used for purposes of illustration and is in no way limiting. Other combinations and/or modifications of the above-described structures, arrangements, applications, proportions, elements, materials, or components used in the practice of the present subject matter, in addition to those not specifically recited, may be varied or otherwise particularly adapted to specific environments, manufacturing specifications, design parameters, or other operating requirements without departing from the general principles of the same.

As used herein, the terms "distal" and "proximal" are understood as positional referents. Objects, elements, and components are "proximal to" or "distal to" one another on the system. "Proximal" refers to a direction toward the system controls and the operator along the path of the catheter system, and "distal" refers to the direction away from the system controls and the operator along the path of the catheter system toward or beyond a terminal end of the operating head.

As used herein, an aspiration source may refer to any device that supplies a negative pressure gradient. The source of negative pressure could be a vacuum pump, peristaltic pump, a diaphragm pump, a piston-based pump, a high-speed water jet disposed at a proper angle and orientation to create a favorable negative pressure gradient, or a simple syringe. All variations are understood to fall within the scope and spirit of the present invention.

As used herein, the term "occlusion" refers to both partial vessel occlusion and complete vessel occlusion. Examples of partial vessel occlusion include a vessel that is narrowed by hardened substances, such as plaque. Additionally, as used herein, the "complete" removal of an occlusion is understood as an effective removal of occlusive material, e.g., a thrombus. Occlusive material may escape removal, while a person having ordinary skill in the art would characterize the removal as complete in that the device has restored patency to the vessel.

As used herein, the term "catheter system" refers to a system configured to remove occlusive material from a body passage, such as a blood vessel. In the examples described herein, the catheter system has been exemplified as a thrombectomy catheter system. However, for the avoidance of doubt, the examples described herein are not limited to use as an instrument for the removal of thrombus from a body passage. Indeed, the examples described herein may be used for the removal of any appropriate occlusive material from a body passage, including, but not limited to, thrombus, atheroma, etc.

FIG. 1 illustrates a perspective view of a thrombectomy catheter system 100. System 100 includes specialized catheter or sheath catheter 102 attached to base unit 107 that houses motorized components (e.g., a controller, an aspiration pump, a clot collection container, etc.) that are operated by a user to effectuate working internal components (not visible in FIG. 1) of specialized catheter or sheath catheter 102 of system 100. A distal end 102a of the sheath catheter 102 is inserted into a vein, artery, or other passageway, advanced to a treatment site, and then deployed to mechanically disrupt, fragment, and aspirate a target substance(s) from the passageway. Helical cutting instrument 101 is disposed at a distal end of sheath catheter 102 and extends axially from an opening 103 at the distal end of sheath catheter 102. Helical cutting instrument 101 has a substantially spherical element having a rounded shape at its distal end serving as an atraumatic tip (as will be described in greater detail below) which reduces the risk that the passageway or the surface of a vessel or tissue will be damaged by the advancement of helical cutting instrument 101 through opening 103 of the sheath catheter 102. Opening 103 permits substance(s) from the patient's body to enter an aspiration lumen formed in the sheath catheter 102. The helical cutting instrument 101 also extends axially from the opening 103. A proximal end 104 of sheath catheter 102 is coupled to a motor 105 that provides rotational and/or reciprocal axial motions to internal components of sheath catheter 102, as discussed in greater detail below. The proximal end 104 of sheath catheter 102 is in fluid communication with an aspiration source, such as pump 106, that provides a negative pressure gradient (e.g. vacuum suction) which draws and the target substance(s) through opening 103 and into the aspiration lumen of the sheath catheter 102. Other known aspiration sources may be used within the scope of this disclosure. Together, the negative pressure gradient and the mechanical fragmentation ensure the efficient and effective removal of substances from the body. In alternative examples, system 100 may include more than one pump or valve in fluid communication with system 100. Such pumps and valves may provide or remove fluids in a way that alters the pressure within system 100. System 100 may be controlled by an ergonomically shaped handle (not illustrated in FIG. 1) that houses motor 105 and either houses or is in fluid contact with pump 106. This allows the user to easily control and manipulate system 100.

Figure 2A:
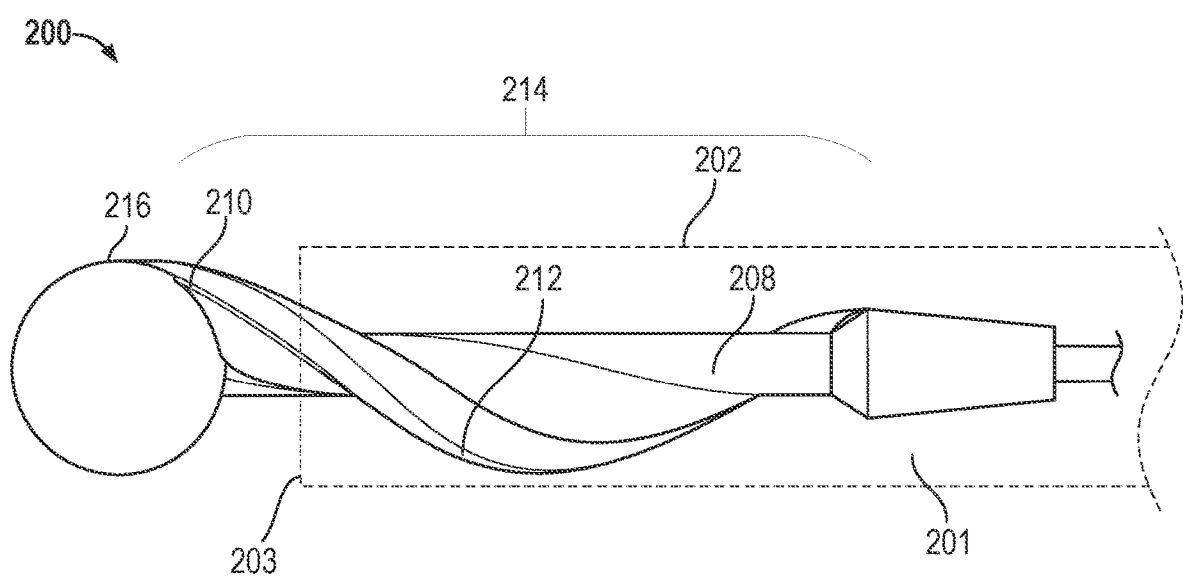
FIG. 2A shows a side detail view of a helical cutting instrument at a distal most segment of the thrombectomy catheter system, in accordance with some examples of the disclosure.

FIG. 2A shows a side detail view of a helical cutting instrument at a distal most segment of the thrombectomy catheter system, in accordance with some examples of the disclosure. The sheath catheter 202 of distal region 200 is shown as transparent (dashed lines) in order to facilitate an understanding of internal components. Distal region 200 of sheath catheter has an opening 203 from which the helical cutting instrument 201 axially extends from. Helical cutting instrument 201 includes a helical body 214 connected to a substantially spherical element 216 which serves as an atraumatic tip. The helical body 214 of helical cutting instrument 201 has a twisted, spiral shape, like a corkscrew, surrounding a central cylindrical shaft 208, as illustrated in FIG. 2A. Helical body 214 includes a pair of edges 210 and 212 on the twisted spiral shape surrounding the central cylindrical shaft 208. In one example, the pair of edges 210 and 212 are each substantially sharpened, or otherwise configured to promote cutting of the target substance upon coming in contact. In another example, one of the edges 210, 212 is substantially sharpened while the other of the edges 210, 212 remains substantially blunt. In this configuration, when the helical body 214 is rotated, the substantially blunt edge is configured to gently pull on or draw in the target substance, while the substantially sharp edge is configured to slice or cut a small portion of the target substance upon coming in contact with the target substance.

Figure 2B:
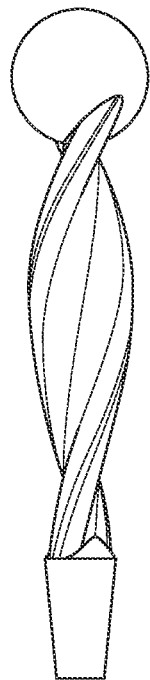
FIGS. 2B-2D show a side view of the helical cutting instrument of the thrombectomy catheter system, in accordance with some examples of the disclosure.
Figure 2C:
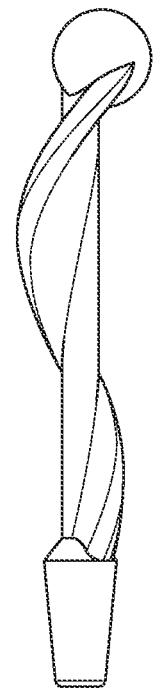
Figure 2D:
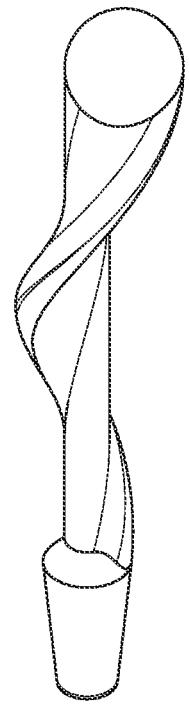

FIGS. 2B-2D show additional views of helical cutting instrument 201 illustrated in FIG. 2A. FIG. 2B shows a front view of the helical cutting instrument 201. Specifically, as shown in FIG. 2B, the helical body 214 of helical cutting instrument 201 has a double helix shape which includes the two edges 210, 212, running opposite to each other and twist together. Although the example illustrated in FIG. 2B does not include cylindrical shaft 208, in another example, the double helical structure may be twisted around the cylindrical shaft 208. FIG. 2C shows a side view of the helical cutting instrument, FIG. 2D shows an isometric view of the helical cutting instrument 201, in accordance with one example of the disclosure.

Figure 2E:
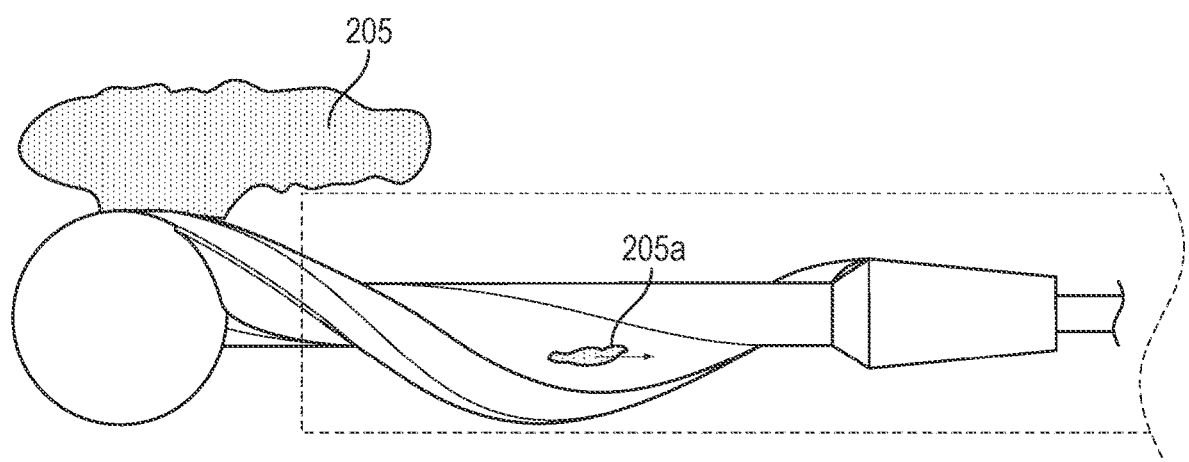
FIG. 2E shows a side, transparent, detail view of the helical cutting instrument in operation, in accordance with some examples of the disclosure.

FIG. 2E shows a side, transparent, detail view of the helical cutting instrument in operation, in accordance with some examples of the disclosure. As illustrated in FIG. 2E, distal end of sheath catheter 202 is positioned proximal to a target substance 205. Motor 105 selectively provides rotational and/or axial motion to the helical cutting instrument 201 once sheath catheter 202 is positioned adjacent to the target substance to distally advance (usually while simultaneously rotating or rotationally oscillating) the helical cutting instrument 201 to extend from the distal end of sheath catheter 202. The substantially spherical element 216 serves as an atraumatic tip upon initial contact with the target substance 205. Specifically, the rounded, atraumatic distal substantially spherical element 216 allows for the safe advancement of the helical cutting instrument 201 through a diseased vessel or a targeted tissue.

In operation, once the substantially spherical element 216 of helical cutting instrument 201 is past the target substance 205, the target substance 205 comes in contact with the pair of rotating edges 210, 212 of helical body 214. As discussed above, in an example, the pair of edges 210 and 212 are each substantially sharpened and are configured to cut a piece of target substance 205 upon coming in contact as they rotate. Specifically, the target substance 205 is subjected to shearing forces by edges 210, 212, as the helical body 214 is being rotated or rotationally oscillated that cuts or slices the target substance 205. In another example, only one of the edges 210, 212 is substantially sharpened while the other of the edges 210, 212 remains substantially blunt. In this configuration, when the helical body 214 is rotated, the substantially blunt edge is configured to gently pull on or draw in the target substance 205, while the substantially sharp edge is configured to slice or cut a small portion 205a of the target substance 205 upon coming in contact.

The resulting fragments are then drawn into the lumen of sheath catheter 202 using a plurality of mechanisms working individually and/or cooperatively. Specifically, as further illustrated in FIG. 2E, as the double helical structure of helical body 214 is rotated, the distal end (i.e., the end connected to the substantially spherical element 216) scoops up the cut portion 205a of target substance 205 and moves it along the surface of helical body 214 towards a proximal end of the helical cutting instrument 201. For instance, in one example, the helical surface of the helical body provides a sliding channel for the cut portion 205a of the target substance 205 to be deposed from the distal section to the proximal section of the catheter 202. In another example, the helical surface of the helical body may include a grooved portion configured to provide a sliding channel for the cut portion 205a of the target substance 205. Moreover, the cut portion 205a of target substance 205 is further drawn into the lumen of sheath catheter 202 by an aspiration source (such as pump 106 in FIG. 1) that provides a negative pressure gradient within the lumen of sheath catheter 202. The cut portion 205a of target substance 205 are drawn into and through the sheath catheter lumen to a proximal region of sheath catheter 202 where they may be removed from the body of the patient.

In this way, the substances (e.g., fragments cut from tissues or clots) are broken up within the system and ingested, while aspiration ensures that minimal, if any, residual substance is permitted to escape evacuation. Once the target substance 205 or portion 205a thereof is inside the lumen of the sheath catheter 202, aspiration draws the substance through the lumen and into a collection chamber (not pictured).

A motor which axially advances and retracts the helical cutting instrument 201 along the lumen of the catheter and which may also simultaneously rotate or rotationally oscillate the helical cutting instrument 201 within the lumen of the catheter will typically be attached to a proximal end of the sheath catheter, as shown for example in FIG. 1, and may be housed in an ergonomically designed handle. The aperture may be formed in a separate structure at the distal end of the sheath catheter, such as in a separate housing. For example, the separate housing may be a metal or rigid polymeric tube having the aperture formed therein. In some examples, the helical cutting instrument 201 is a separate device from the sheath catheter and the helical cutting instrument 201 may be rotated as well as axially advanced and retracted separately and independently from the sheath catheter. The catheter may act as a sheath to the helical cutting instrument 201 in some examples.

While the examples shown in FIGS. 2A-2E illustrate a helical cutting instrument 201 having double helix shaped edges, it is understood that the edges may take any appropriate form. Indeed, the cutting instrument 201 may comprises any appropriate number of edges, such as a single edge, or any multiple number of edges, e.g., depending on the configuration of the cutting instrument 201 and/or its intended operational purpose. In some examples, the cutting instrument may comprise at least one edge having a varying amount of curvature, e.g., the edge may comprise at least one straight portion (e.g., axially aligned portion) and at least one curved portion. In some examples, the edge may be a spiraled edge having a constant or varied pitch. In some examples, the radial height of the edge may be constant or varied along the length of the body 214. In some examples, the edge may extend radially outwards, e.g., perpendicularly, from a longitudinal axis of the body 214, e.g., for at least a portion of a length of the edge. In some examples, the edge may be raked forwards or backwards, e.g., inclined to or from, a longitudinal axis of the body 214, e.g., for at least a portion of a length of the edge. For the avoidance of doubt, the term "helical", when applied to the examples described herein, is not intended to be limiting and is used for the sake of example. Indeed, the present disclosure envisages that the benefits of the cutting instrument described herein may be achieved with any appropriately configured edge or edges of the cutting instrument 201.

Figure 3A:
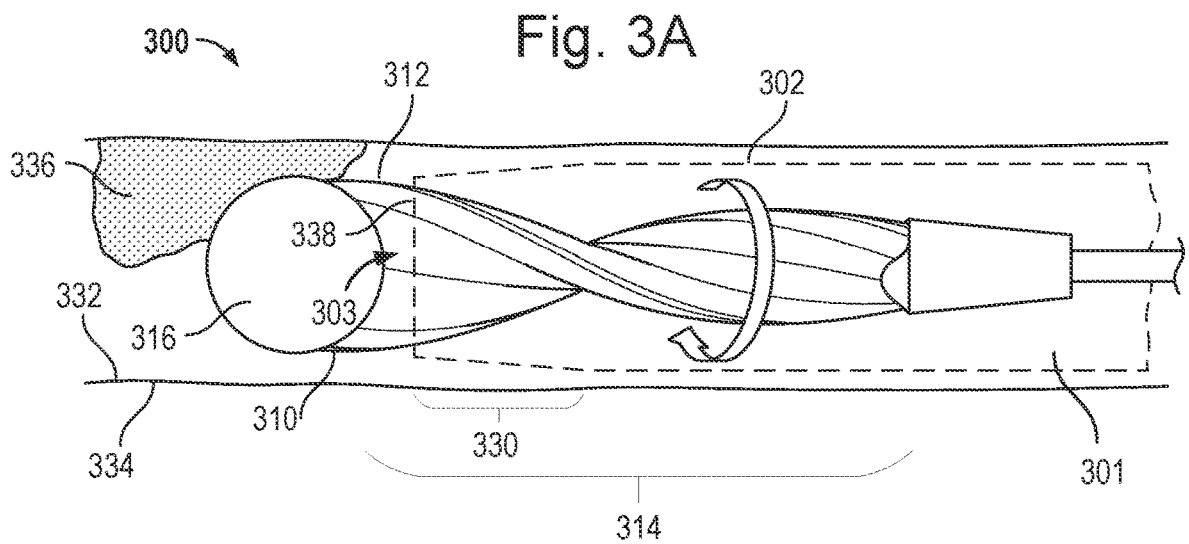
FIGS. 3A-3C show a side detail view of another implementation of a helical cutting instrument having a tapered sheath, in operation, in accordance with some examples of the disclosure.
Figure 3B:
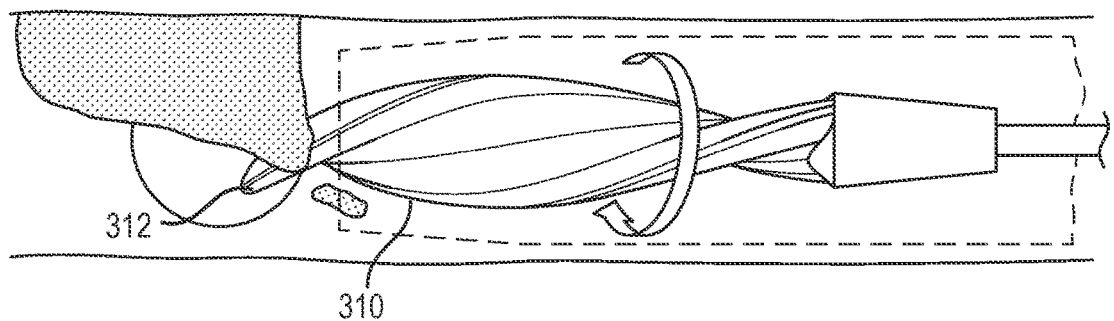
Figure 3C:
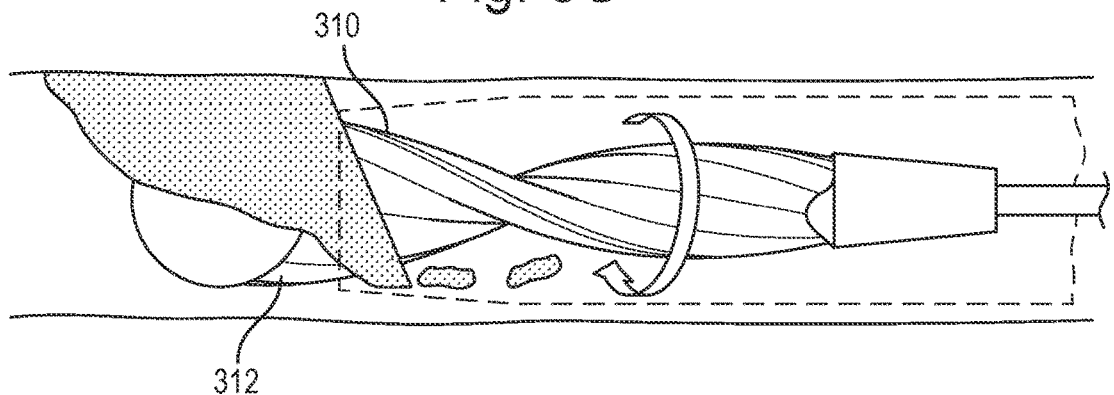

FIGS. 3A-3C show side detail views of a helical cutting instrument at a distal most segment of the thrombectomy catheter system, in accordance with some examples of the disclosure. The sheath catheter 302 of distal region 300 is shown as transparent (dashed lines) in order to facilitate an understanding of internal components. Distal region 300 of sheath catheter has an opening 303 from which the helical cutting instrument 301 is axially extendable. Helical cutting instrument 301 includes a helical body 314 connected to a substantially spherical element 316, which serves as an atraumatic tip. In the example shown in FIGS. 3A-3C, sheath catheter 302 further comprise a distally tapered portion 330, causing a radial gap/offset between the helical cutting instrument 301 and the sheath 302 to reduce towards opening 303. In some examples, distally tapered portion 330 may be configured such that the size of opening 303 closely matches the size of the helical cutting instrument 301, e.g., the diameter of the substantially spherical element 316.

In the example shown in FIGS. 3A-3C, the distally tapered portion 330 tapers by a shallow angle, e.g., 2 degrees or 5 degrees. However, in other examples, the tapered portion 330 may taper by any appropriate angle, such as 10 degrees, 30 degrees, or more, and may extend over any appropriate length of the sheath catheter 302. Importantly, irrespective of the value of the taper angle of tapered portion 330, a reduction in the radial size of the distal region 300 of sheath catheter 302 assists in the implantation of the helical cutting instrument 301. For example, a reduction in the radial size of the distal region 300 of sheath catheter 302 helps mitigate the distal region 300 of sheath catheter 302 becoming snagged and/or otherwise causing damage to an inner wall 332 of a body lumen 334, e.g., during the advancement of the distal region 300 of sheath catheter 302 towards a clot 336. As such, the risk of tissue injury due to helical cutting instrument 301 as shown in FIGS. 3A-3C may be reduced during placement at a clot site by virtue of cooperation between substantially spherical element 316 and tapered portion 330, e.g., by substantially matching the diameter of opening 303 to the diameter of the substantially spherical element 316. For example, the radial gap/offset between the substantially spherical element 316 and opening 303 of tapered portion 330 may be approximately 0.1 mm, and increase therefrom proximally along the sheath catheter 302, e.g., in a liner or non-linear manner.

Similar to the example shown in FIGS. 2A-2E, the helical body 314 of helical cutting instrument 301 has a twisted, spiral shape, like a corkscrew, and helical body 314 includes a pair of edges 310 and 312 on the twisted spiral shape. However, in the example shown in FIGS. 3A-3C, edge 310 is substantially sharpened, or otherwise configured to promote cutting of the target substance upon coming in contact, while edge 312 remains substantially blunt. In this configuration, when the helical body 314 is rotated, the substantially blunt edge 312 is configured to gently pull on or draw in the target substance while the substantially sharp edge 310 is configured to slice or cut a small portion of the target substance upon coming in contact with the target substance, and/or upon interaction with an edge 338 at least partially forming distal opening 303 of sheath catheter 302. FIGS. 3A-3C illustrate three operational states, e.g., snapshots, which show a cutting mechanism implemented by helical cutting instrument 301.

In FIG. 3A, helical cutting instrument 301 has been advanced through body lumen 334 to the site of clot 336. Helical cutting instrument 301 has been distally extended from opening 303, such that substantially spherical element 316 impinges on clot 336, and edges 310 and 312 on the twisted spiral shape are no longer covered by sheath 302.

In FIG. 3B, helical cutting instrument 301 has been rotated clockwise by approximately 90 degrees, as viewed looking onto the distal end of the helical cutting instrument 301. As shown, substantially blunt edge 312 acts to pick up a portion of clot 336 and start to draw clot 336 into and through opening 303. In some examples, such an action may cause one or more portions of clot 336 to break off, e.g., without any interaction between clot 336 and substantially sharp edge 310. In some examples, axial reciprocation of helical cutting instrument 301 may promote clot 336 being drawn into opening 303.

In FIG. 3C, helical cutting instrument 301 has been rotated clockwise by approximately another 90 degrees, such that edges 310 and 312 are shown moved by an approximate half turn compared to the operational state shown in FIG. 3A. In FIG. 3C, substantially blunt edge 312 continues to draw clot 336 through opening 303 to an extent at which clot 336 engages edge 338 of distal opening 303. In some examples, the action of the pulling of clot 336 by substantially blunt edge 312 urges clot 336 against edge 338 in a manner that causes edge 338 to cut into clot 336. Additionally or alternatively, the action of cutting the clot 336 using the substantially sharp edge 310 may be improved as a result of clot 336 being under tension, owing to the pulling action of substantially blunt edge 312 (e.g., as shown in FIG. 3C). Additionally or alternatively, the action of cutting the clot 336 using substantially sharp edge 310 may be improved as a result of a shearing action between the substantially sharp edge 310 and edge 338 of the distal opening 303 of sheath catheter 302. Such a shearing action may be promoted by a close operational clearance between the edges 310, 312 and the inner diameter of the distal end of the sheath 302, which may be implemented by tapering, or otherwise reducing the radial size, of the distal end of sheath 302, as shown in FIGS. 3A-3C.

Figure 4A:
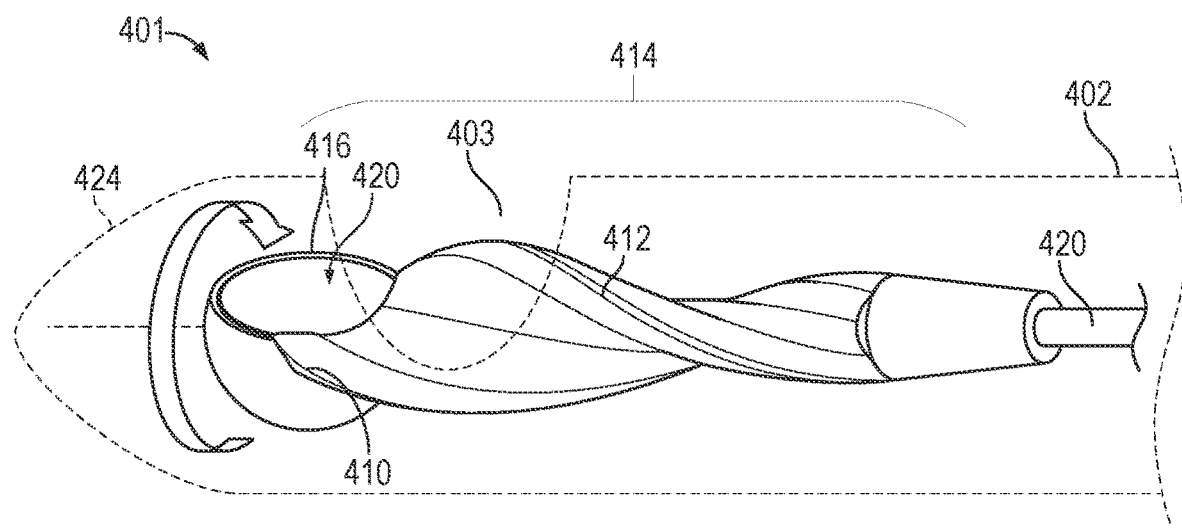
FIG. 4A shows a side detail view of another implementation of the helical cutting instrument, in accordance with some examples of the disclosure.

FIG. 4A shows a side detail view of another implementation of the helical cutting instrument, in accordance with some examples of the disclosure. Helical cutting instrument 401 of FIG. 4A includes a substantially spherical element 416 connected to a helical body 414. The operation of helical body 414 is similar to that of helical body 214 discussed above in connection with FIGS. 2A-2E. The substantially spherical element 416 of helical cutting instrument 401 differs from substantially spherical element 216 of helical cutting instrument 201 in that the substantially spherical element 416 includes a scooped-out portion 420. In an example, an edge portion of the scooped-out portion 420 is substantially sharpened or otherwise configured to promote cutting of the target substance as the substantially spherical element 416 comes in contact with the target substance (while simultaneously being rotated or rotationally and laterally oscillated). Moreover, as further illustrated in FIG. 4A, the scooped-out portion 420 is designed to open into the helical body 414 of the helical cutting instrument 401. This allows for any sliced or cut portions of the target substance to be moved proximally along the helical body 414 (e.g., via a central channel or central surface, which may be substantially flat and/or smooth) by leveraging the helical shape of the helical body 414.

Moreover, as illustrated in FIG. 4A, in some examples, sheath catheter 402 includes an aperture 403 and an atraumatic distal tip 424, which may be softer/more flexible relative to the remainder of the sheath catheter 402. The soft, atraumatic distal tip 424 allows for the safe advancement of the device through the diseased vessel. A substantially sharpened edge of the scooped-out portion 420 is typically serrated or otherwise configured to promote cutting of the target substance as the helical cutting instrument 401 is advanced (and optionally rotated and/or rotationally oscillated). The substantially sharpened edge of the scooped-out portion 420 is configured to promote shearing of the excised portion of the target substance from the remaining mass of target substance as the leading edge engages the target substance.

The aperture 403 is typically formed as a "side window" in the distal region of the sheath catheter 402, and the helical cutting instrument 401 may be advanced and retracted to adjust the size of a gap between the cutting body and the distal end of the window. Aspiration pulls the target substance, such as clot material, to the open window, and the rotating helical cutting instrument 401 fragments the clot as it enters the window. A motor which rotates or rotationally oscillates the helical cutting instrument 401 will typically be attached to a proximal end of the sheath catheter, as shown for example in FIG. 1, and may be housed in an ergonomically designed handle. The aperture may be formed in a separate structure at the distal end of the sheath catheter, such as in a separate housing. For example, the separate housing may be a metal or rigid polymeric tube having the aperture formed therein. In some examples, both the sheath catheter and the helical cutting instrument are substantially flexible and pliable.

Figure 4D:
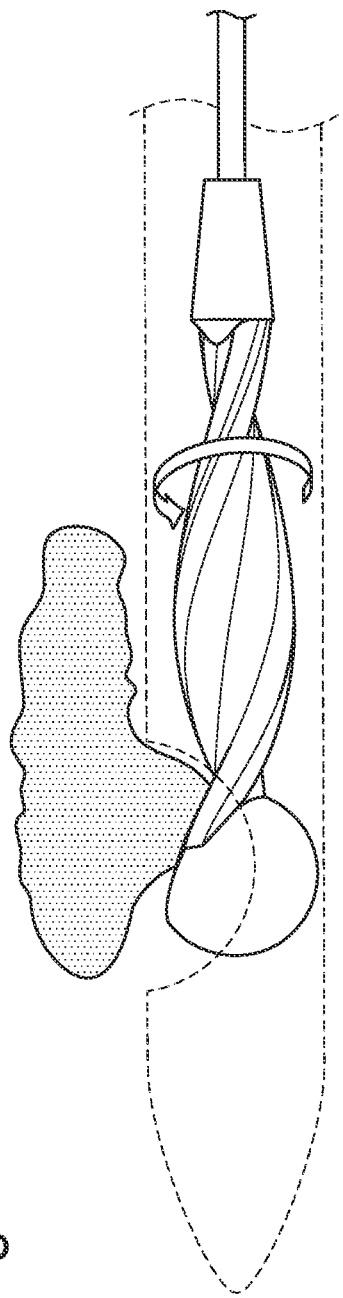
Figure 4E:
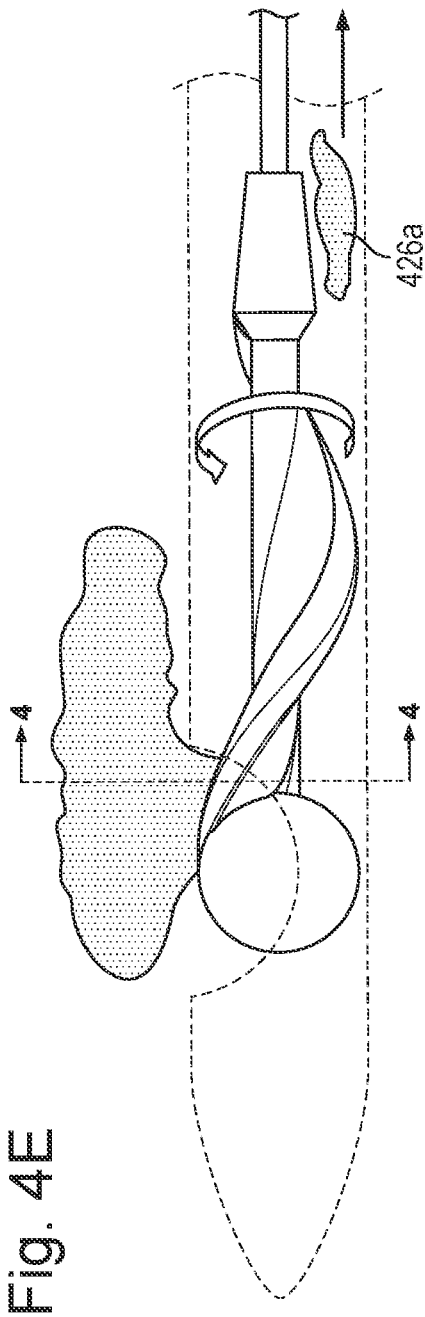

FIGS. 4B-4E show a side, transparent, detail view of the helical cutting instrument 401 in operation, in accordance with some examples of the disclosure. FIG. 4B illustrates a system 400 at a first point in time, when system 400 is in a first configuration, prior to beginning the rotational movement of the helical cutting instrument 401. FIG. 4C illustrates system 400 at a second point in time, when system 400 is in a second configuration, during a first rotation of the helical cutting instrument by thirty degrees from its initial position shown in FIG. 4B. FIG. 4D illustrates system 400 at a third point in time, when system 400 is in a third configuration, during a second rotation of the helical cutting instrument by an additional thirty degrees from its position shown in FIG. 4C. FIG. 4E illustrates system 400 at a fourth point in time, when system 400 is in a fourth configuration, during a third rotation of the helical cutting instrument by an additional thirty degrees from its position shown in FIG. 4D. For clarity, not all features of a system according to the invention are included in FIGS. 4B, 4C, 4D, and 4E. System 400 includes the helical cutting instrument 401.

Turning to FIG. 4B, the sheath catheter 402 is positioned near the target substance 426. Specifically, sheath catheter 402 is advanced through the blood vessel with the clot or thrombus until the soft, atraumatic conical tip 424 contacts and then pushes past the target substance 424. In some examples, the catheter 402 does not include the atraumatic tip 424 and the aperture 403. Instead, the sheath catheter 402 has an open distal end from which the helical cutting instrument is configured to axially extend and retract from. The target substance 426 is pulled into the aperture 403 by the aspirating source (e.g., pump 106). Next, helical cutting instrument 401 positioned inside a lumen of the sheath catheter 401 is distally advanced until the substantially spherical element 416 of helical cutting instrument 401 contacts the target substance 426. As shown in FIG. 4B, a rounded atraumatic portion of the substantially spherical element 416 initially contacts the target substance 426.

Next, as illustrated in FIG. 4C, the helical cutting instrument 401 is rotated and/or rotationally oscillated such that the target substance 426 is pulled inside the scooped-out portion 420. In other words, the rotation of the helical cutting instrument 401 (in combination with an aspiration source) applies a pulling force on the target substance 426 to draw in the target substance 426 within the scooped-out portion 420.

Turning now to FIG. 4D, the helical cutting instrument 401 is rotated and/or rotationally oscillated in order to apply a shearing force onto the target substance 426. More particularly, an edge portion of the scooped-out portion 420 is substantially sharpened or otherwise configured to promote cutting of the target substance. When the shearing force is applied onto the target substance 426 by the substantially sharpened edge of the scooped-out portion 420, the target substance is sheared, cut, sliced, and/or fragmented.

FIG. 4E shows the discrete and relatively uniform slicing or shearing of the target substance due to the rotational shearing force applied on the target substance. The axial and rotational motion of the helical cutting instrument 401, which ultimately places the cutting edge of the scooped-out portion 420 and the cutting edges 410, 412 of the helical body 414 into contact with the target substance 426, causes the shearing or slicing of target substance 426.

As the helical cutting instrument 401 moves axially while simultaneously rotating or rotationally oscillating, target substance 426 may be sliced into smaller portions. This slicing creates a discrete and relatively uniform fragment, which is then immediately aspirated, in part by the helical structure of the helical body 414. As the helical cutting instrument 401 slices or cuts the target substance, the cut portion generated is aspirated along the helical body 414 (e.g., by way of a channel surface of the helical body) in a proximal direction. The relatively uniform fragments 426a are then further aspirated in a proximal direction (indicated by the arrow) within the sheath catheter's lumen. This fragmentation occurs within the sheath catheter's lumen, and thereby reduces the risk of clot fragment dispersal within the patient's vasculature.

Figure 5:
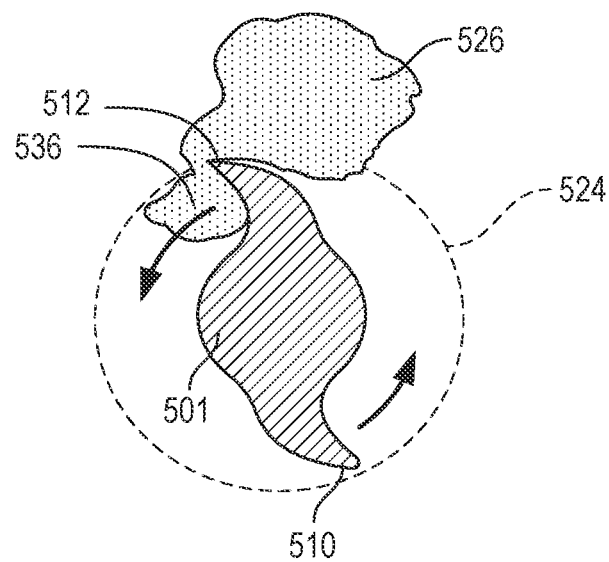
FIG. 5 shows a cross-section of the helical cutting instrument of FIG. 4A, in accordance with some examples of the disclosure.

FIG. 5 shows a cross-section of the helical cutting instrument of FIG. 4E along line 4-4, in accordance with some examples of the disclosure. As illustrated in FIG. 5, as the helical cutting instrument 501 is rotated or rotationally oscillated within a lumen of sheath catheter 524, a shearing force is applied on the target substance 526 by edges 510, 512 of the helical cutting instrument 501. The shearing force applied by the edges 510, 512 of the helical cutting instrument 501 causes target substance 526 to be sliced. This slicing creates a discrete and relatively uniform fragment 536, which is then aspirated along the helical body of the helical cutting instrument 501 in a proximal direction.

Although FIG. 5 shows an anti-clockwise rotation of the helical cutting instrument 501, in other examples, the helical cutting instrument 501 can be rotated in a clockwise direction. In one example, edge 510 of the helical cutting instrument 501 is substantially blunt while edge 512 of the helical cutting instrument 501 is substantially sharpened, or otherwise configured to promote cutting of the target substance 526. When the edge 510 first comes into contact with the target substance 526, instead of cutting or slicing the target substance, edge 501 pulls onto a fragment (e.g., fragment 536) of the target substance 526 into the lumen of the sheath catheter. Continued rotation of the helical cutting instrument 501 causes substantially sharpened edge 512 to come into contact with the fragment 536 which then proceeds to cut or slice that fragment. In this manner, the two different edges 510, 512 work together to slice small discrete portions of the target substance 526, while preventing damage to the blood vessels.

Figure 6:
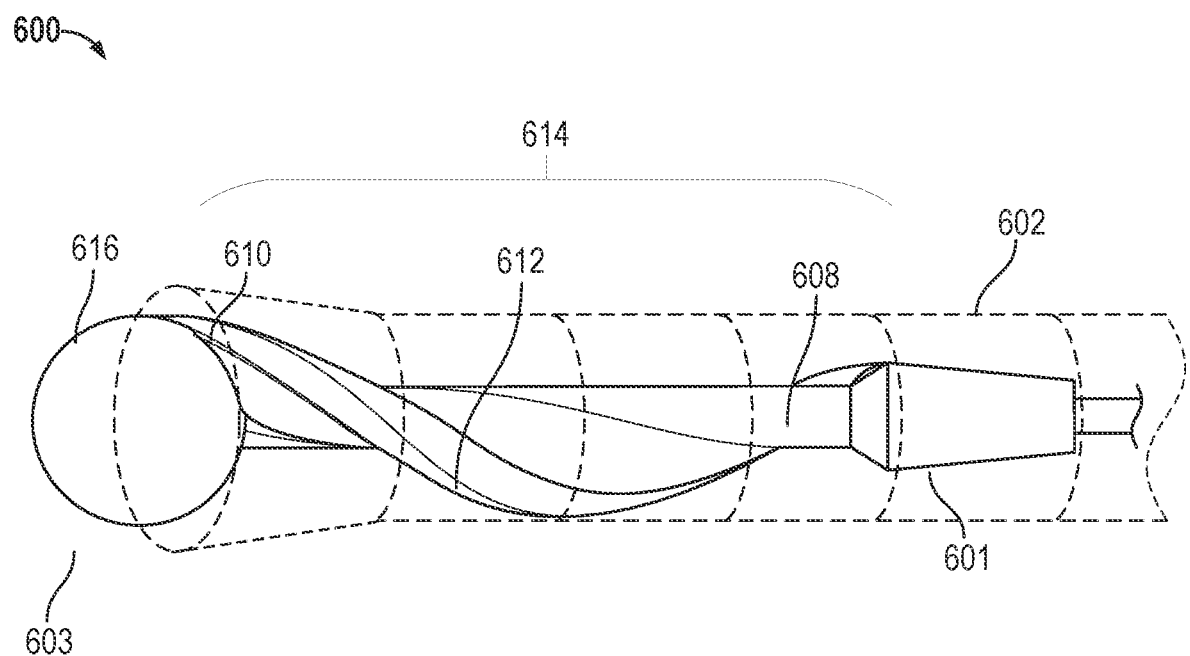
FIG. 6 shows a side detail view of a helical cutting instrument at a distal most segment of the thrombectomy catheter system, in accordance with some examples of the disclosure.

FIG. 6 shows a side detail view of a helical cutting instrument at a distal most segment of the thrombectomy catheter system, in accordance with some examples of the disclosure. The sheath catheter 602 of distal region 600 is shown as transparent (dashed lines) in order to facilitate an understanding of internal components. Distal region 600 of sheath catheter 602 has an opening 603 from which the helical cutting instrument 601 is axially deployable/retractable. Helical cutting instrument 601 includes a helical body 614 connected to a substantially spherical element 616 which serves as an atraumatic tip. The helical body 614 of helical cutting instrument 601 has a twisted, spiral shape, like a corkscrew, surrounding a central cylindrical shaft 608, as illustrated in FIG. 6. Helical body 614 includes a pair of edges 610 and 612 on the twisted spiral shape surrounding the central cylindrical shaft 608. In one example, at least one of the pair of edges 610 and 612 is configured to promote removal of the target substance, e.g., by cutting, upon engaging the target substrate. In some examples, at least one of the pair of edges 610 and 612 may be configured to sever a portion of the target substance by urging the target substrate against the catheter sheath 602, e.g., against an inner wall of the catheter sheath 602 and/or an edge of an opening in a wall of the catheter sheath 602.

As illustrated in FIG. 6, the distal end of sheath catheter 602 is flared, e.g., conical in shape, and is positionable proximal to a target substance. While the flared portion of the catheter sheath 602 is shown in FIG. 5 as a conical portion, the flared portion maybe any appropriately shaped portion that results in the transverse area of the catheter sheath 602 increasing along its length, e.g., toward its distal end. This sheath tip can be optimized to maximize force on clot given steady vacuum. It can also be optimized to protect the vessel wall from the cutting portion of the helical cutting instrument. A motor, such as motor 105 of FIG. 1, selectively provides rotational and/or axial motion to the helical cutting instrument 601, e.g., once sheath catheter 602 is positioned adjacent to the target substance, to distally advance (usually while simultaneously rotationally driving) the helical cutting instrument 601 to extend from the distal end of sheath catheter 602. The substantially spherical element 616 serves as an atraumatic tip upon initial contact with the target substance. Specifically, the rounded, atraumatic distal element 616 allows for the safe advancement of the helical cutting instrument 601 through a diseased vessel or a targeted tissue without damaging a wall of the vessel.

The flared shape of the distal end of catheter sheath 602 comprises an opening 603 that is controllably opened and/or closed. In one example, the opening 603 (and/or the overall shape of the flared portion) is controlled by virtue of a shape memory filament (not shown). For example, catheter sheath 602 may comprise one or more heat-set filaments that cause the distal end of the catheter sheath 602 to change from a first state, e.g., where the opening 603 of the catheter sheath 602 is closed, or at least narrowed compared to the transverse size of the helical body 614, to a second state, e.g., where the opening 603 of the catheter sheath 602 is open, or at least widened compared to the transverse size of the helical body 514. In some examples, the shape of the distal end of catheter sheath 602 maybe changed from a tapered shaped, such as that shown in FIGS. 3A-3C, to a flared shape, such as that shown in FIG. 6.

In some examples, a change in state, e.g., physical dimensions, of the shape memory filament in the distal end of the catheter sheath 602 may be caused by removal or retraction of one or more restraint elements (not shown) configured to restrain the shape memory filament, e.g., in the first state, as the catheter sheath 602 is being advanced through a vessel towards a target occlusion. In some examples, the one or more restraint elements may comprise an outer sheath or band (not shown) extending at least circumferentially around the catheter sheath 602, e.g., at or towards the distal end of the catheter sheath 602. The outer sheath may axially slidable relative to the catheter sheath 602, such that retraction of the outer sheath relative to the catheter sheath 602 causes the shape memory filament to change from the first state to the second state.

In some examples, the catheter sheath 602 may comprise one or more expandable elements (not shown), e.g., balloon elements, positioned at or towards the distal end of the catheter sheath 602, which cause the distal end of the catheter sheath 602 to radial expand or flare, thus widening opening 603, upon inflation of the one or more expandable elements. In one example, widening of the opening 603 is at least partially caused by the axial movement, e.g., distal extension, of cutting instrument 601 relative to catheter sheath 602.

In FIG. 6, the cutting instrument 601 is shown in a partially extended position, such that the opening 503 is opened to allow the spherical element 616 to extend beyond the distal end of the catheter sheath 602. In some examples, the shape of the distal end of the catheter sheath 602 and/or opening 603 is controlled by one or more control wires (not shown), e.g., that can be manipulated to cause opening 603 to widen, resulting in the transverse cross-sectional area of the catheter sheath 602 increasing towards its distal end. In use, the opening 603 of the catheter sheath 602, in its expanded state, may be in contact with the inside wall of the of the blood vessel in which it is implanted. The flared shape of the distal end of the catheter sheath 602, as shown in FIG. 6, aids in removing the target substance, such as a clot, from the blood vessel wall by funneling the target substance towards the spherical element 616 and helical cutting instrument 601, e.g., as shown in more detail in FIGS. 11A-11C. In addition, the flared shape of the distal end of the catheter sheath 602, aids in reducing trauma to the vessel walls by the cutting instrument 601, in particular the advancement of the substantially spherical element 616, by centering the cutting instrument 601 relative to the vessel walls.

In the example shown in FIG. 6, the flared portion is shown as extending from the distal end of the catheter sheath 602. However, in another example, the catheter system may comprise a secondary catheter sheath (not shown) extending around catheter sheath 602. In such an example, the secondary catheter sheath may comprise a flared portion similar to that described above, either alone, or in combination with a flared portion of catheter sheath 602.

Figure 7:
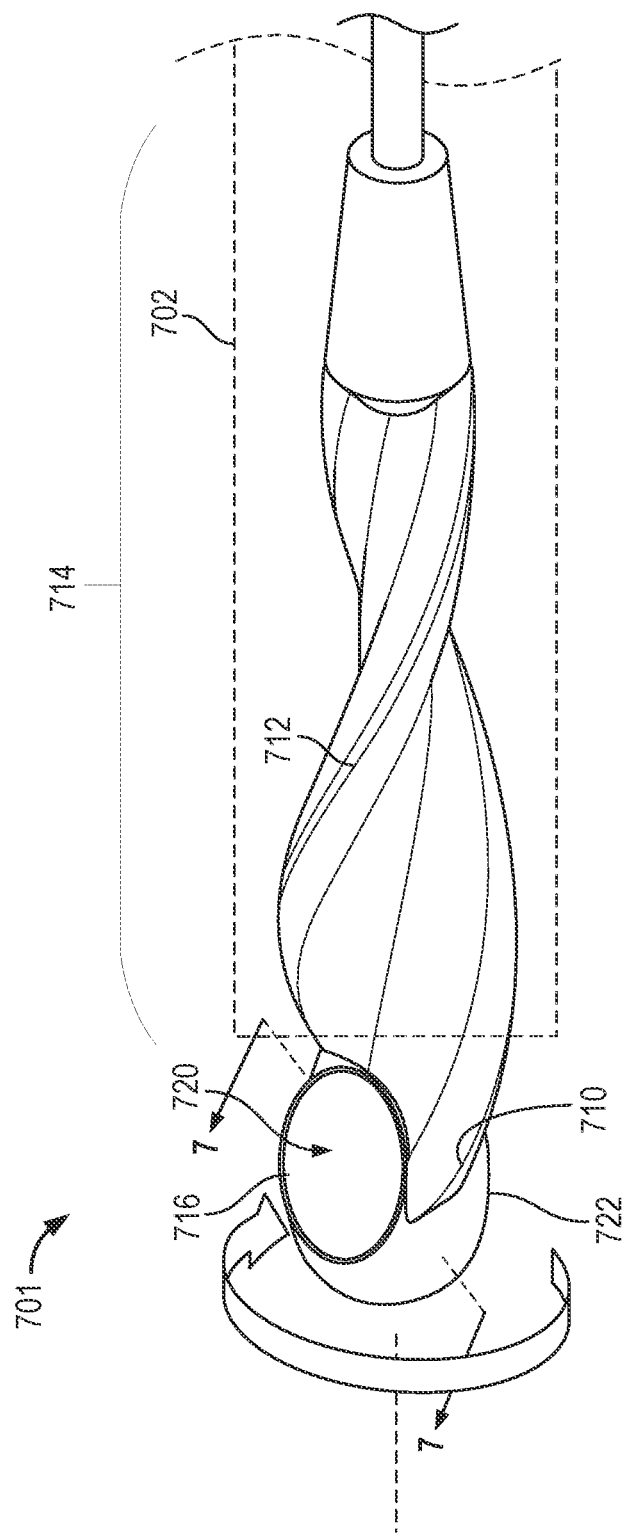
FIG. 7 shows a side detail view of another implementation of the helical cutting instrument, in accordance with some examples of the disclosure.

FIG. 7 shows a side detail view of another implementation of a helical cutting instrument 701, in accordance with some examples of the disclosure. Helical cutting instrument 701 of FIG. 7 includes a substantially spherical element 716 connected to a helical body 714 having edges 710, 712. The operation of helical body 714 is similar to that of helical bodies 214 and 314 discussed above in connection with FIGS. 2A-2E and 3A-3E. The substantially spherical element 716 of helical cutting instrument 701 differs from substantially spherical element 216 of helical cutting instrument 201 and substantially spherical element 316 of helical cutting instrument 301 in that the substantially spherical element 716 includes two scooped-out portions 720, 722. In an example, the scooped-out portions 720, 722 are on opposite sides of the helical cutting instrument 701 with a rounded top portion connecting the two scooped-out portions. As shown in FIG. 7, the scooped-out portion 720 is designed to open into the helical body 714 of the helical cutting instrument 701. This allows for any sliced or cut portions of the target substance to be moved proximally along the helical body 714 by leveraging the helical shape of the helical body 714. Scooped-out portion 722 (shown in FIG. 8) similarly opens up into an opposite side of the helical body 714.

In an example, edge portions of the scooped-out portions 720, 722 are substantially sharpened or otherwise configured to promote cutting of the target substance as the substantially spherical element 716 comes in contact with the target substance (while simultaneously being rotated or rotationally oscillated). In one example, only one of the edges of the scooped-out portions 720, 722 is substantially sharpened while the other of the edges of the scooped-out portions 720, 722 is substantially blunt. This configuration allows for one of the scooped-out portions 720, 722 with the substantially blunt edge to pull on the target substance to draw the target substance into the cutting path of the other scooped-out portion and the rotating or rotationally oscillating helical body 714.

Figure 8:
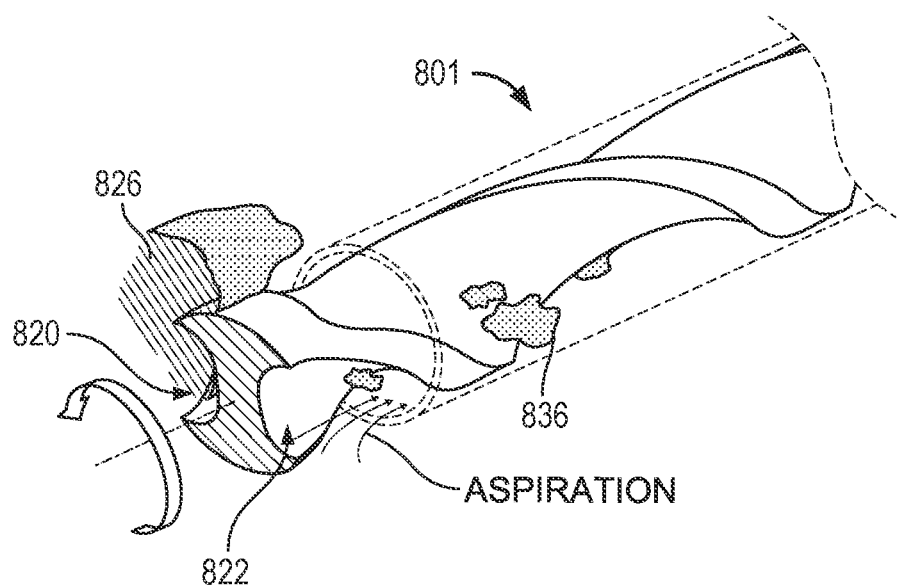
FIG. 8 shows a perspective cross-section of the helical cutting instrument of FIG. 7, in accordance with some examples of the disclosure.

FIG. 8 shows a cross-section of the helical cutting instrument of FIG. 7 along line 7-7, in accordance with some examples of the disclosure. As illustrated in FIG. 8, as the helical cutting instrument 801 is rotated or rotationally oscillated, a shearing force is applied on the target substance 826 by the scooped-out portions 820, 822 of the helical cutting instrument 801. The shearing force applied by the scooped-out portions 820, 822 of the helical cutting instrument 801 causes target substance 826 to be sliced. This slicing creates a discrete and relatively uniform fragment 836, which is then immediately aspirated along the helical body of the helical cutting instrument 801 in a proximal direction. Although FIG. 8 shows an anti-clockwise rotation of the helical cutting instrument 801, the helical cutting instrument 801 can be rotated in a clockwise direction in other examples. In one example, scooped-out portion 822 of the helical cutting instrument 801 has a substantially blunt edge while scooped-out portion 820 of the helical cutting instrument 801 has a substantially sharpened edge, or is otherwise configured to promote cutting of the target substance 826. When the scooped-out portion 822 first comes into contact with the target substance 826, instead of cutting or slicing the target substance, scooped-out portion 822 merely pulls onto a fragment (e.g., fragment 836) of the target substance 826. Continued rotation of the helical cutting instrument 801 causes scooped-out portion 820 with the substantially sharpened edges to come into contact with the fragment 836 which then proceeds to cut or slice that fragment. In this manner, the two scooped-out portions 820, 822 work together to slice small discrete portions of the target substance 826, while preventing damage to the blood vessels.

Figure 9A:
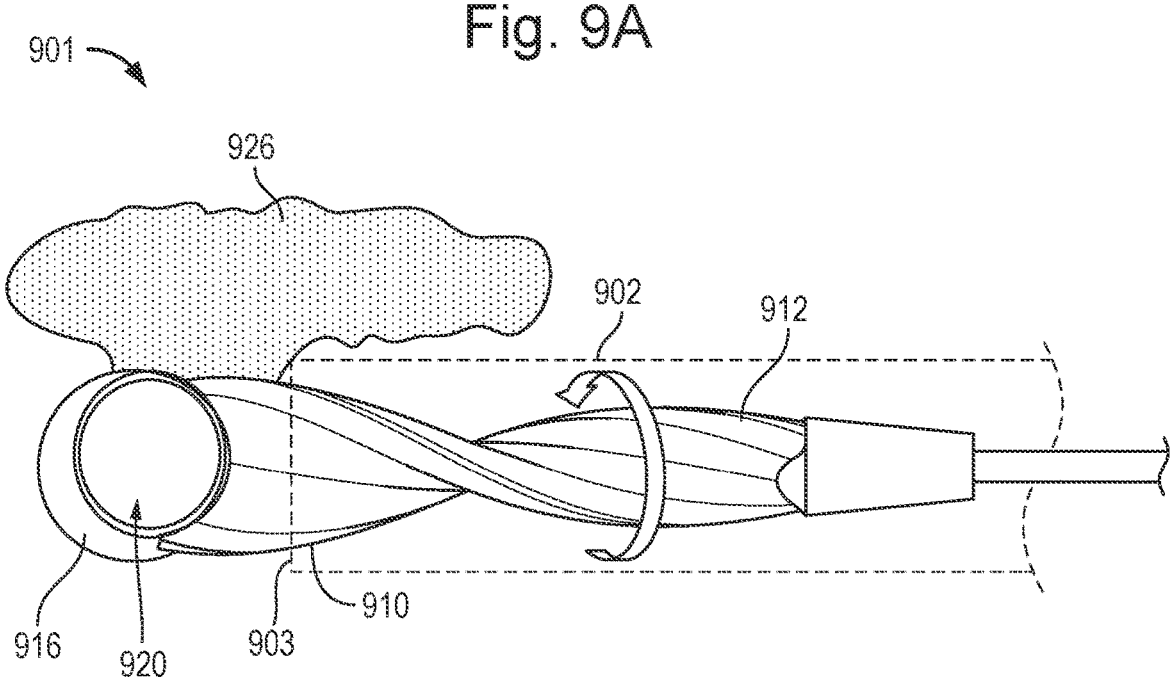
FIGS. 9A-9C show a side, transparent, detail view of the helical cutting instrument of FIG. 7, in operation, in accordance with some examples of the disclosure.
Figure 9B:
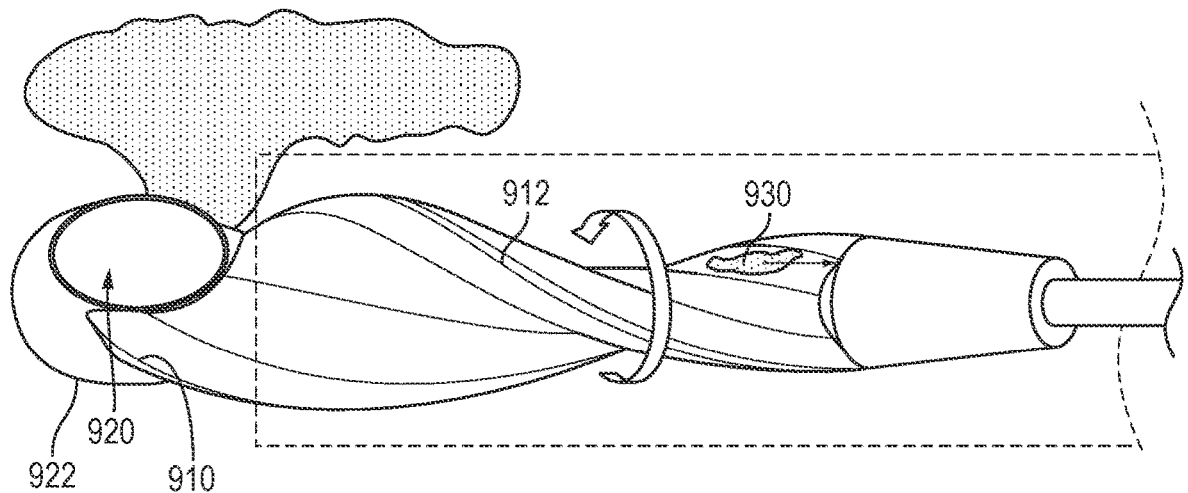
Figure 9C:
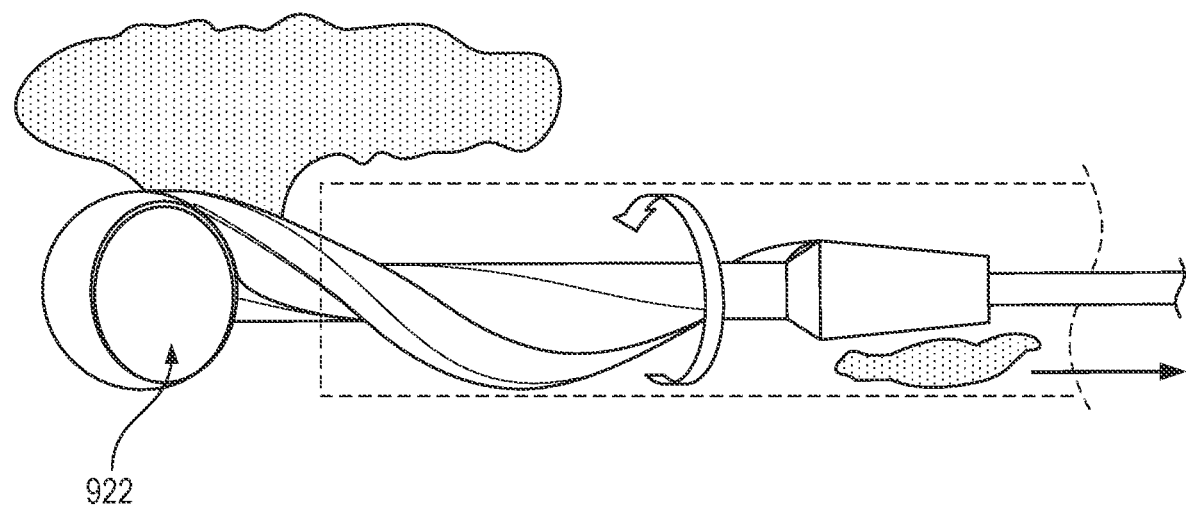

FIGS. 9A-9C show a side, transparent, detail view of the helical cutting instrument 701 of FIG. 7 in operation, in accordance with some examples of the disclosure. FIG. 9A illustrates a system at a first point in time, when the system is in a first configuration, prior to beginning the rotational movement of the helical cutting instrument 901. FIG. 9B illustrates the system at a second point in time, when the system is in a second configuration, during a first rotation of the helical cutting instrument by ninety degrees from its initial position shown in FIG. 9A. FIG. 9C illustrates the system at a third point in time, when the system is in a third configuration, during a second rotation of the helical cutting instrument by an additional ninety degrees from its position shown in FIG. 9B. For clarity, not all features of a system according to the invention are included in FIGS. 9A, 9B, and 9C. The system includes the helical cutting instrument 901.

Turning to FIG. 9A, the sheath catheter 902 is positioned near the target substance 926. Specifically, sheath catheter 902 is advanced through the blood vessel with the clot or thrombus until the sheath catheter opening 903 is adjacent to the target substance 926. Next, helical cutting instrument 901 is distally advanced outside a lumen of the sheath catheter 901 from opening 903 until the substantially spherical element 916 of helical cutting instrument 901 contacts the target substance 926. As shown in FIG. 9A, a rounded atraumatic portion of the substantially spherical element 916 makes the initial contact with the target substance 926 so as to prevent any damage to the blood vessels while the helical cutting instrument 901 is being positioned. At this time, the scooped-out portion 922 faces the target substance 926 such that rotation of the helical cutting instruments imparts a shearing force onto the target substance 926.

Next, as illustrated in FIG. 9B, the helical cutting instrument 901 is rotated and/or rotationally oscillated such that the target substance 926 is sliced by the scooped-out portion 922. In other words, the rotation of the helical cutting instrument 901 (in combination with an aspiration source) applies a pulling force on the target substance 926 to draw it inside the scooped-out portion 922 and then applies a shearing force by an edge of the scooped-out portion 922 as the helical cutting instrument 901 continues its rotation. The application of the shearing force by the edge of the scooped-out portion 922 causes shearing or slicing of the target substance 926 resulting in smaller fragments 930 being collected in the scooped-out portion 922. As discussed above, the scooped-out portion 922 opens up into the helical body of the helical cutting instrument 901 which allows the fragment 930 to be moved proximally into the lumen of the sheath catheter (e.g., by way of a channel surface of the helical body), from which it is further aspirated in a proximal direction.

Turning now to FIG. 9C, the helical cutting instrument 301 is rotated and/or rotationally oscillated an additional ninety degrees such that it is rotated 180 degrees from its position in FIG. 9A. At this point of time, the scooped-out portion 920 faces the target substance 926 such that rotation of the helical cutting instruments imparts a shearing force onto the target substance 926, while the scooped-out portion 922 faces away the target substance 926. Accordingly, additional rotation of the helical cutting instrument 901 causes an edge of the scooped-out portion 920 to slice the target substance 926. The rotation of the helical cutting instrument 901 (in combination with an aspiration source) applies a pulling force on the target substance 926 to draw it inside the scooped-out portion 920 and then applies a shearing force by an edge of the scooped-out portion 920 as the helical cutting instrument 901 continues its rotation. The application of the shearing force by the edge of the scooped-out portion 920 causes fragmenting of the target substance 926 resulting in smaller fragments 930 being collected in the scooped-out portion 920. As discussed above, the scooped-out portion 920 also opens up into the helical body of the helical cutting instrument 901 which allows the fragment 930 to be moved proximally into the lumen of the sheath catheter, from which it is further aspirated in a proximal direction.

In an example, each of the scooped-out portion 920, 922 include a leading substantially blunt edge portion which first contacts the target substance 926 and applies a pulling force onto the target substance 926. The scooped-out portion 920, 922 also each include a trailing substantially sharp edge portion which contacts the target substance 926 after the leading substantially blunt edge and applies a shearing or cutting force onto the target substance 926. Thus, the leading substantially blunt edge and the trailing substantially sharp edge work together to pull a fragment of the target substance 926 and then perform a cutting action.

Figure 10:
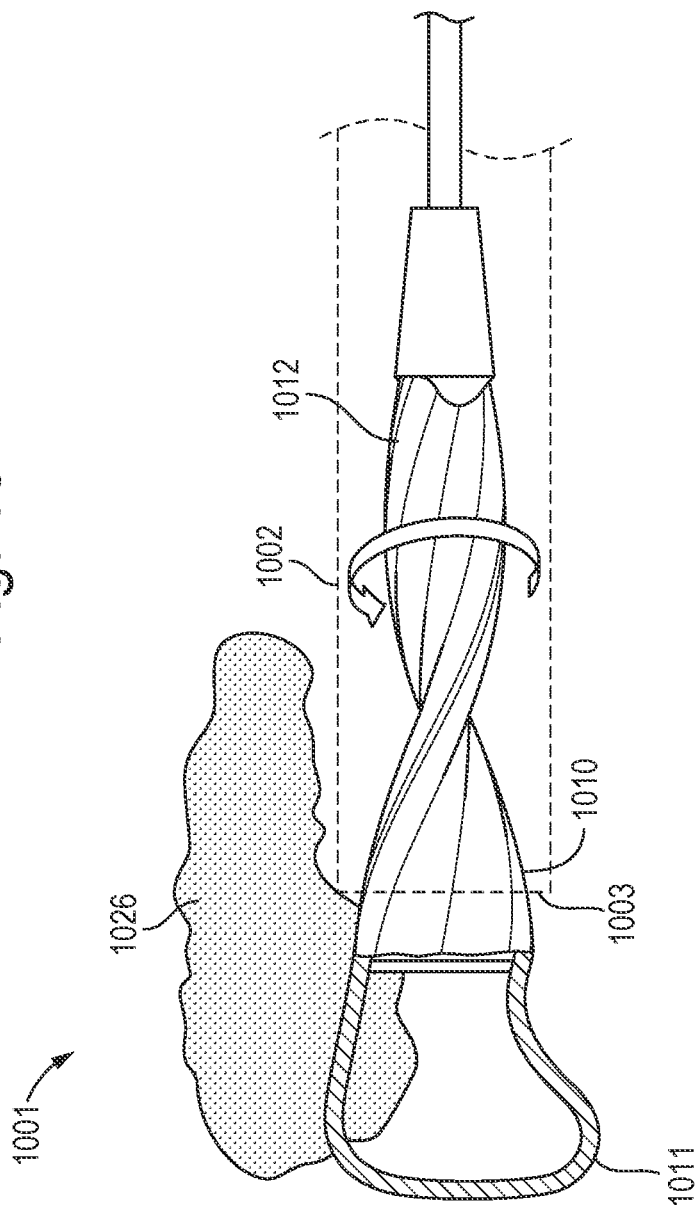
FIG. 10 shows a side detail view of another implementation of the helical cutting instrument having a looped tip, in accordance with some examples of the disclosure.

FIG. 10 shows a side, transparent, detail view of a helical cutting instrument with an atraumatic wire element 1011, in accordance with some examples of the disclosure. While FIG. 10 shows wire element 1011 replacing substantially spherical element, it is understood that wire element 1011 may be used in combination with substantially spherical element, as described in relation to the FIGS. As illustrated in FIG. 10, distal end of sheath catheter 1002 is positioned proximal to a target substance 1026. A motor, such as motor 105, selectively provides rotational and/or axial motion to the helical cutting instrument 1001 once sheath catheter 1002 is positioned adjacent to the target substance to distally advance (usually while simultaneously rotating or rotationally oscillating) the helical cutting instrument 1001 to extend from the distal end of sheath catheter 1002 through an opening 1003. In the example shown in FIG. 10, the wire element 1011 extends from edge 1010 to edge 1011. In other examples, the wire element 1011 may comprise a loop, a loop of coiled wire and/or a hook that serve as an atraumatic tip as the cutting instrument 1001 is advanced through a body vessel toward a clot site, e.g., in a similar manner to the substantially spherical element. Specifically, the wire element 1016 allows for the safe advancement of the helical cutting instrument 1001 through a diseased vessel or a targeted tissue, e.g., by virtue of its flexibility and/or resilience, but still enables pulling, cutting and/or slicing of a target substance 1026, or otherwise promotes removal of a target substance 1026 from a body vessel. In some examples, the choice of material of the atraumatic wire element 1011 could include shape memory material that would offer an appropriate balance of flexibility and/or resilience, or a tunable flexibility and/or resilience. For the avoidance of doubt, the example atraumatic wire element 1011 is compatible with any of the examples as described herein.

In operation, the rotating atraumatic wire element 1011 of helical cutting instrument 1001 comes into contact with the target substance 1026. Specifically, the target substance 1026 is subjected to shear force when engaged by the atraumatic wire element 1011, e.g., as the helical body 1014 is rotated or rotationally oscillated. Such forces act to help draw target substance 1026 away from an inner wall of a vessel to which the target substance 1026 is adhered. In some examples, the atraumatic wire element 1011 acts to entangle the target substance 1026 upon rotation of the helical cutting instrument 1001, such that the target substance 1026 is drawn into sheath catheter 1002 upon retraction of helical cutting instrument 1001. Additionally or alternatively, wire element 1011 may be configured to cut into the target substance 1026 upon rotation of the helical cutting instrument 1001. The resulting fragments are then drawn into the lumen of sheath catheter 1002 as describes in relation to the above examples.

Figure 11A:
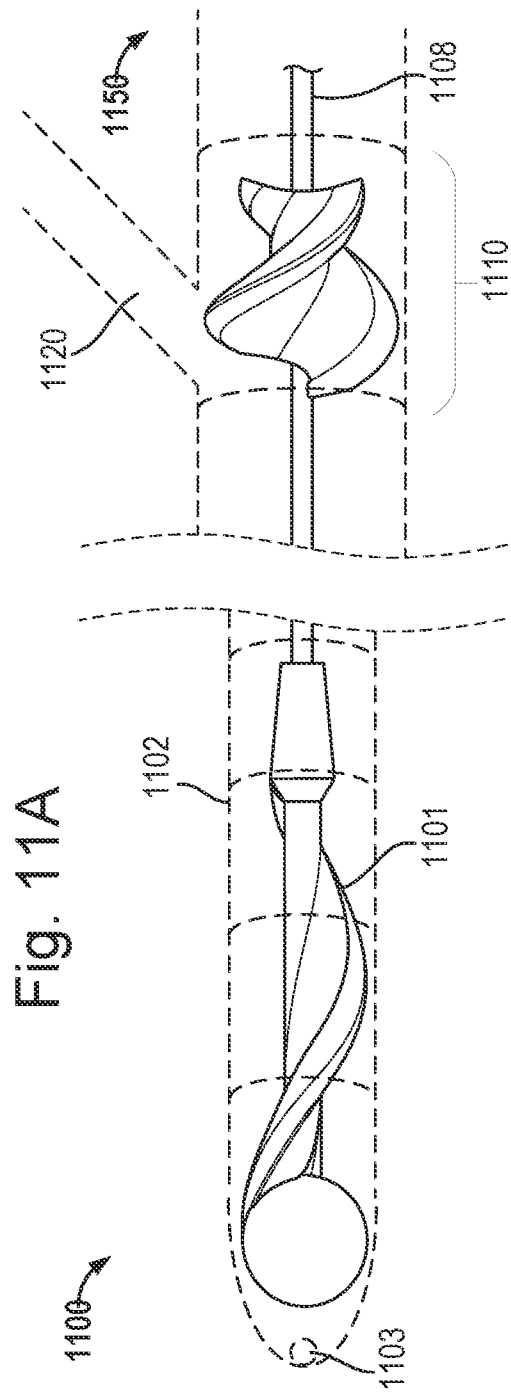
FIGS. 11A-11C show a side detail view of another implementation of the helical cutting instrument with a macerating portion, in accordance with some examples of the disclosure.
Figure 11B:
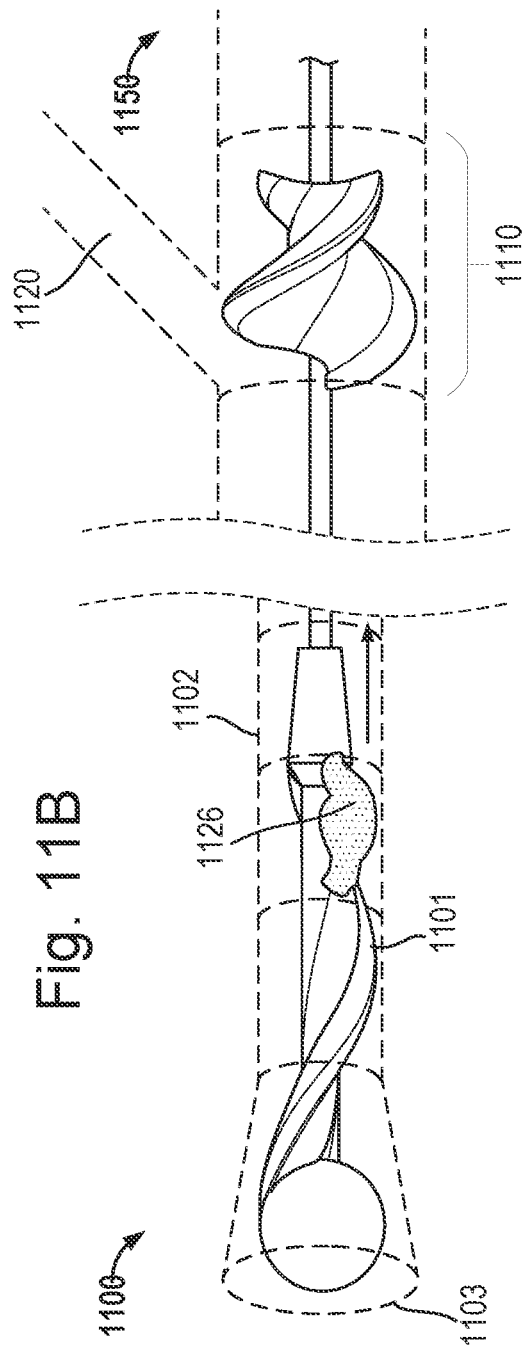
Figure 11C:
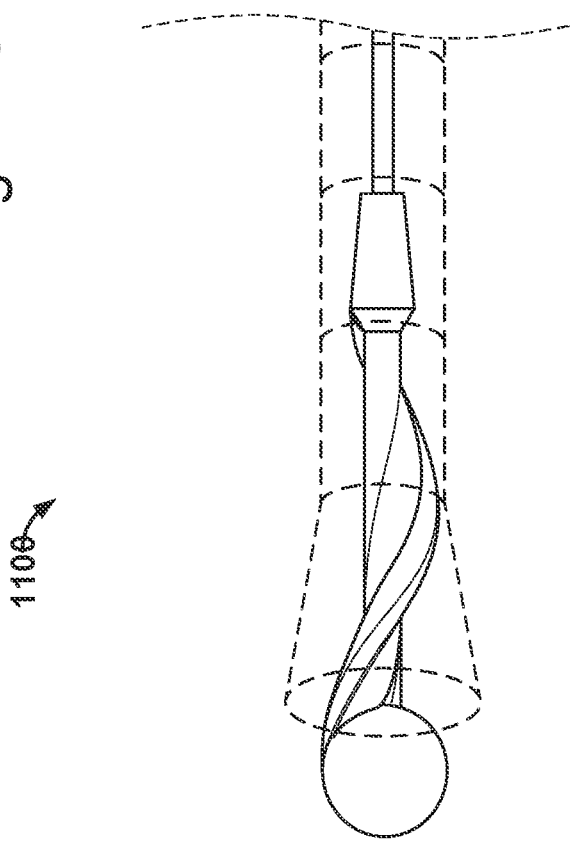

FIGS. 11A-11C show a side detail view of another implementation of the helical cutting instrument, in accordance with some examples of the disclosure. As shown in FIG. 11A, opening 1103 in the distal region 1100 of sheath catheter 1102 is closed/narrow and the cutting instrument 1101 is in a retracted position. FIGS. 11A-11C also depict a macerating portion 1110 of the catheter system 100. The macerating portion 1110 comprises a macerating blade that is coupled to the drive wire/drive shaft 1108 that, in this example, also drives the cutting instrument 1101. As such, the rotational and axial position of the cutting instrument 1101 and the macerating blade are synchronised. The macerating portion 1110 is configured to aid in the breaking apart portions 1126 of the target substance that are aspirated through the sheath catheter 1102. In the example shown in FIGS. 11A-11C, the macerating portion 1110 is disposed adjacent the aspiration tube, such that aspirated portions 1126 of the target substance moving proximally through the sheath catheter 1102 are broken up into smaller pieces to aid entry into and passage through aspiration tube 1120.

In some examples, the size of sheath catheter 1102 of may vary along its length. In particular, as shown in FIGS. 11A-11C, the distal end 1100, comprising the cutting instrument 1101, may be smaller in diameter than the proximal end 1150, comprising the macerating portion 1110. Such a variation in size may be permitted by several reasons. For example, the macerating portion 1110 of catheter system 100 may be configured for ex-vivo operation, and, as such, need not be constrained by factors affecting the portion of the catheter system 100 configured for in-vivo operation (size, heat, toxicity, etc.). As such, the macerating blade of macerating portion 1110 may be configured to break up the aspirated portions 1126 of the target substance in a more aggressive manner than cutting instrument 1101. For example, the macerating blade may be larger, e.g., ½ inch in diameter, and/or have a more aggressive blade angle, e.g., a steeper lead-in angle, than the cutting instrument 1101. In the example shown in FIGS. 11A-11C, the macerating blade is shown as a spiral-shaped blade. However, the macerating blade may have any appropriate configuration for breaking up aspirated portions 1126 of the target substance.

In FIG. 11B, the draft shaft 1108 has been distally advanced, causing cutting instrument 1101 and macerating portion 1110 to advance also. Notably, macerating portion 1110 has advanced, but is still adjacent the aspiration tube 1120. That is to say, the macerating portion 1110, in the most distally advanced position and most proximally retracted position of the drive shaft 1108, at least partially overlaps with the entry to aspiration tube 1120. Also shown in FIG. 11B is a portion of the target substance 1126, which has been removed from the blood vessel and aspirated towards aspiration tube 1120 and macerating portion 1110 by virtue of operation of the cutting instrument 1101 and aspiration pressure. In FIG. 11C the target substance 1126 has been broken into smaller target substance pieces after passing through macerating portion 1110.

Figure 12C:
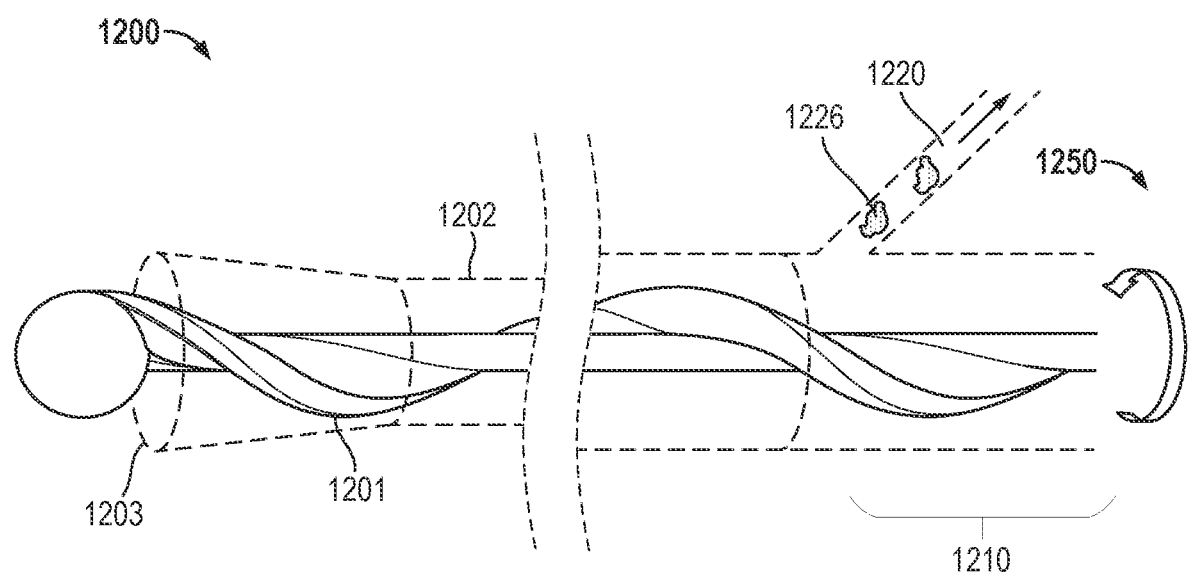

FIGS. 12A-12C show a side detail view of another implementation of the helical cutting instrument, in accordance with some examples of the disclosure. In FIGS. 12A-12C, distal end 1200, cutting instrument 1201, sheath catheter 1202, opening 1203 and proximal end 1250 are like that described for corresponding features in FIGS. 11A-11C. However, macerating portion 1210 is different to macerating portion 1110. For example, macerating portion 1210 comprises a macerating blade having the same, or similar, configuration to the helical body of cutting instrument 1201. In some examples, the helical body of the cutting instrument 1201 may extend, e.g., continuously, from the distal end 1200 to macerating portion 1210. As such, the outer diameter of sheath catheter 1202 may remain constant, e.g., between a distal portion of the catheter system configured for in-vivo operation and a proximal portion of the catheter system configured for ex-vivo operation. In some examples, the pitch, rake, and/or the outer dimensions of the helical body of cutting instrument 1201 may vary along its length. For example, the pitch of the helical body of cutting instrument 1201 may increase and/or the outer diameter of the helical body may decrease along at least a portion of the helical body between the distal end 1200 and the proximal end 1250. The removal, aspiration, and break-up of target substance 1226 may occur in a similar manner to that described for the example of FIGS. 11A-11C.

Figure 13A:
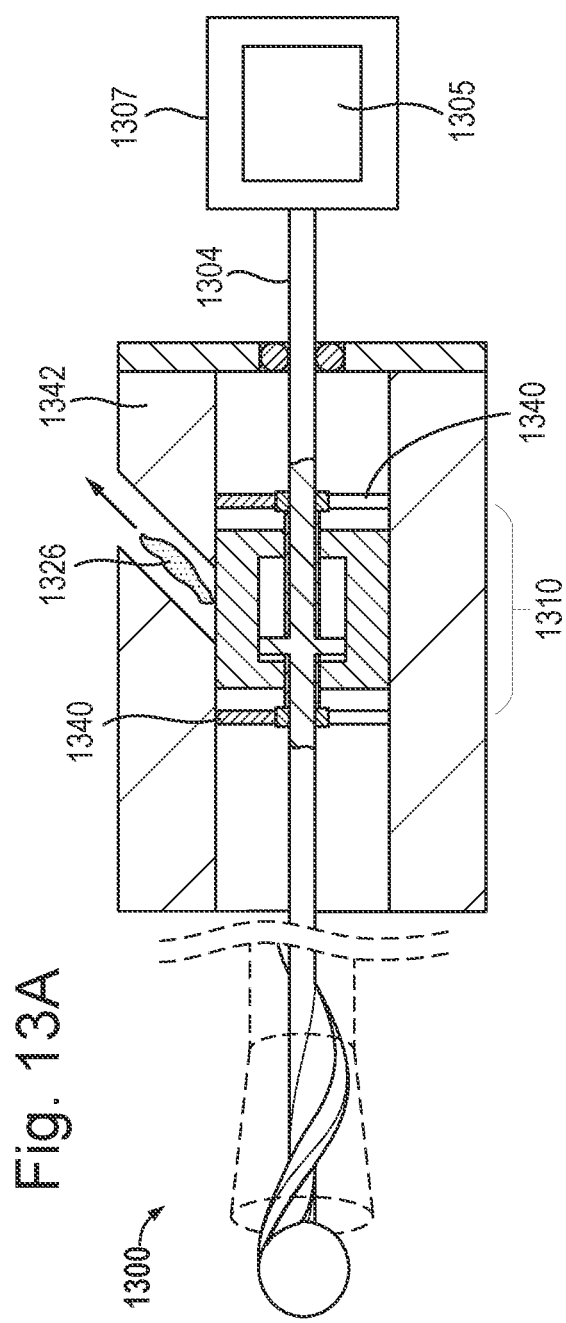
FIG. 13A shows a cross-section of a macerating portion of another implementation of the catheter system, in accordance with some examples of the disclosure.
Figure 13B:
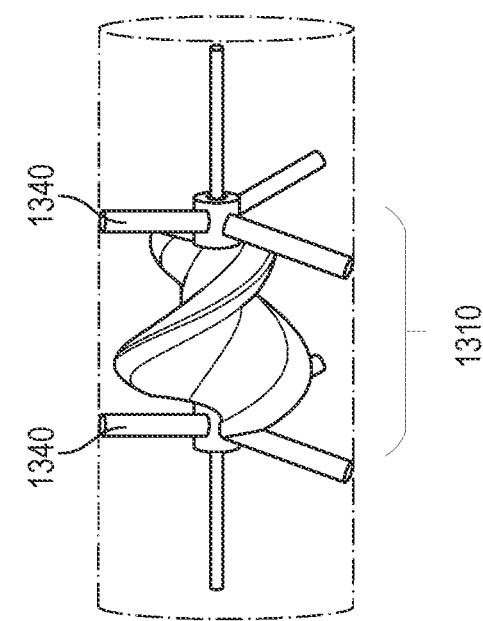
FIG. 13B shows a side detail view of the macerating portion of FIG. 11A, in accordance with some examples of the disclosure.

FIG. 13A shows a cross-section of a macerating portion of another implementation of the catheter system, in accordance with some examples of the disclosure, and FIG. 13B shows a side detail view of the macerating portion of FIG. 13A, in accordance with some examples of the disclosure. In FIGS. 13A and 13B, the distal end 1300 is similar to the distal end of any of the above-described examples. However, in the example shown in FIGS. 13A and 13B, macerating portion 1310 comprises a macerating blade that is mounted on or around drive shaft 1304 in a manner that transfers rotational drive from the drive shaft 1304 to the macerating blade and allows for axial movement of the drive shaft 1304 relative to the macerating blade. For example, the macerating blade may be supported by one or more support structures 1340 within a housing 1342 of macerating portion 1310. For example, FIG. 13B shows two support structures 1340, each having a hub and three equally spaced support legs arranged circumferentially around the hub.

As shown in FIG. 13A, the support structures 1340 carry the macerating blade such that the macerating blade is axially restrained within housing 1342 and can rotate about a longitudinal axis. Drive shaft 1304 extends from motor 1305 and base unit 1307, through a wall of housing 1342 and central openings in the support structures 1340 and the macerating blade. In some examples, the drive shaft 1304 and macerating blade are rotationally coupled, e.g., by virtue of a key feature or spine, that transfers rotational drive from the drive shaft to the macerating blade. In this manner, the macerating blade spins at the same rotational speed as the drive shaft 1304 (and thus the cutting instrument). Additionally, the coupling between the drive shaft 1304 and macerating blade allows for the drive shaft 1304 to slide, e.g., distally and proximally, relative to macerating blade and housing 1342. In the example shown in FIG. 13A, drive shaft 1304 is shown in a distally extended position, such that the cutting instrument protrudes from distal end 1300 and the key feature or spine is moved to a distal extent of its travel within the macerating portion 1310. In some examples, base unit 1307 and housing 1342 may be is configured for ex-vivo operation and fixable to a benchtop in a manner that allows catheter sheath 1302 to be removably secured to an inlet to housing 1342. In such an example, base unit 1307 and housing 1342 may be reusable and/or serviceable portions of the catheter system, whereas any portions of the catheter system coupled distally to the housing 1342 may be single use items.

FIG. 14 shows a cross-section of a macerating portion of another implementation of the catheter system, in accordance with some examples of the disclosure. In FIG. 14, distal end 1400 is similar to the distal end of any of the above-described examples. However, in the example shown in FIG. 14, macerating portion 1410 comprises a macerating blade that is mounted on driveshaft 1444, which is separate from drive shaft 1404. In the example shown in FIG. 14, drive shaft 1404 and 1444 are arranged in a coaxial arrangement such that drive shaft 1404 extends through the macerating blade and drive shaft 1444. In this manner, the helical cutter and the macerating blade can be controlled independently from each other, e.g., so that they can be driven at different rotational speeds. Such an implantation is beneficial as it allows for the speed of the macerating blade to be greater than the speed of the helical cutter, which preserves the gentle action of the helical cutter against a wall of a vessel, and allows for high shear forces to be generated in the macerating housing 1442, which optimizes aspiration of target substance 1426 through the aspiration tube. In the example shown in FIG. 14, drive shaft 1404 and drive shaft 1444 are coupled to motor 1405 and base unit 1407. However, in one or more other examples, drive shaft 1404 and drive shaft 1444 may be coupled to respective motors and/or drive units (controllers). An apparatus according to the present disclosure can include catheters adapted for intraluminal introduction into the target body lumen. The dimensions and other physical characteristics of the catheter will vary significantly depending on the body lumen which is to be accessed. In the case of catheters intended for intravascular introduction, the catheter will typically be flexible and may be compatible with introduction over a guidewire to a target site within the vasculature. In particular, catheters can be intended for "over-the-wire" introduction when a guidewire lumen extends fully through the catheter body or for "rapid exchange" introduction where the guidewire lumen extends only through a distal portion of the catheter body.

Benefits, advantages, and solutions to problems have been described above with regard to particular examples. However, any particular benefit, advantage, or solution is not to be construed as critical, required, or essential. Nor is any particular element that may cause or amplify a benefit, advantage, or solution to be construed as critical, required, or essential.

The examples illustrated have been described to promote clarity of understanding, and it will be obvious that any equivalent modifications will fall within the scope of the appended claims. Equivalent modifications are understood to include, but not be limited by, the following examples: (1) performing the steps recited in a method in any order or skipping steps altogether, (2) varying dimensions and materials within reasonable limits, (3) varying the configuration of elements in way that achieves substantially the same result, and (4) combining different examples in a way that achieves substantially the same result.

The present disclosure, and the examples illustrated herein, makes substantial, non-obvious improvements over the conventional systems and methods for aspirating a clot. In particular, the examples in accordance with the subject matter disclosure herein fragment target substances in a discrete, bite-like manner. The complimentary geometries of the substantially spherical element and the helical body enables the helical cutting instrument to efficiently cut a clot into smaller portions and aspirate the resulting fragments into a lumen of a catheter without expelling them into the vasculature. The fragmentation occurs safely within a defined space. The discrete fragments are immediately aspirated further within the device's lumen. The cycle of cutting the substance and aspirating a fragment is then repeated. This improves on prior art where the devices fragment target substances within the vasculature, whereby the fragments are simultaneously dispersed throughout the vasculature. Such dispersal can cause further complications that the present invention avoids. The present examples do not release fragments within the vasculature. The creation of the fragments is simultaneous with their removal. The fragments are thereby immediately removed, rather than dispersed into the patient's vasculature.

What is claimed is:

1. An aspiration thrombectomy system comprising:
    an aspiration catheter having a proximal end and a distal end, wherein the aspiration catheter comprises a lumen configured to accommodate fluid;
    an aspiration source configured to provide a negative pressure gradient to alter a level of pressure in the aspiration thrombectomy system to draw occlusive material into the aspiration catheter;

a plurality of valves in fluid communication with the aspiration thrombectomy system, wherein one or more of the valves are configured to provide or remove fluids to alter the level of pressure in the aspiration thrombectomy system; and a cutting instrument associated with the distal end of the aspiration catheter,
  wherein the cutting instrument comprises a spiral body connected to a substantially spherical element having a scooped-out portion,
  wherein a distal point of the substantially spherical element is configured to be an atraumatic tip,
  wherein the scooped-out portion is configured to engage with the target occlusive material at a proximal point of the substantially spherical element,
  wherein the cutting instrument is configured for one or more motions comprising one or more of axial motion and rotational motion, and
  wherein the aspiration thrombectomy system is configured to cut and remove the target occlusive material based on the one or more motions of the cutting instrument and changes to the level of pressure in the aspiration thrombectomy system.

2. The system of claim 1, wherein the cutting instrument is configured to distally advance outside of the lumen of the catheter.

3. The system of claim 1, wherein the cutting instrument is configured to proximally retract inside of the lumen of the catheter.

4. The system of claim 1, wherein the axial motion comprises a reciprocal axial motion.

5. The system of claim 1, wherein the rotational motion comprises a rotationally oscillating motion.

6. The system of claim 1, further comprising at least one motor operatively coupled with the cutting instrument, wherein the at least one motor is configured to impart one or more of the rotational motion and the axial motion to the instrument.

7. The system of claim 1, wherein the cutting instrument includes a central smooth surface configured to depose a cut portion of the target occlusive material from a distal end of the spiral body to a proximal end of the spiral body.

8. The system of claim 1, wherein the spiral body comprises a plurality of helical structures.

9. The system of claim 1, wherein a maximum diameter of the substantially spherical element substantially matches a diameter of the lumen at the distal end of the aspiration catheter.

10. The system of claim 1, wherein the scooped-out portion includes an edge at a proximal point of the substantially spherical element configured to promote cutting of the target occlusive material.

11. The system of claim 10, wherein the scooped-out portion includes a leading substantially blunt edge at a first proximal point of the substantially spherical element configured to pull at least a portion of the target occlusive material into the scooped-out portion and a trailing substantially sharpened edge at a second proximal point of the substantially spherical element configured to promote cutting of the target occlusive material.

12. The system of claim 1, wherein the substantially spherical element includes a plurality of scooped-out portions at a plurality of respective proximal points of the substantially spherical element.

13. The system of claim 12, wherein each of the scooped-out portions comprises:
  a leading substantially blunt edge at a first proximal point of the substantially spherical element configured to pull at least a portion of the target occlusive material into the respective scooped-out portion; and
  a trailing substantially sharpened edge at a second proximal point of the substantially spherical element configured to promote cutting of the target occlusive material.

14. The system of claim 1, wherein the atraumatic tip is configured to make initial contact with the target occlusive material to prevent damage to a vasculature of a patient.

15. The system of claim 1, wherein an opening of the distal end of the aspiration catheter is configured to operate in a plurality of operational states, and wherein one or more of the operational states are associated with a cross-sectional size of the opening or a shape of the opening.

16. The system of claim 1, wherein the aspiration thrombectomy system is configured to allow fluid communication between the distal end of the aspiration catheter and the aspiration source.

17. The system of claim 1, wherein changing the level of pressure is configured to move at least a portion of the target occlusive material through the lumen towards a proximal region of the aspiration catheter.

18. The system of claim 17, wherein the cutting instrument is configured to fragment the target occlusive material, and wherein the fragmenting of the target occlusive material is confined within the lumen of the aspiration catheter based at least in part on a helical structure of the cutting instrument and the changing of the level of pressure in the aspiration thrombectomy system.

19. The system of claim 1, wherein the cutting instrument further comprises a macerating portion positioned adjacent to an internal junction of the aspiration catheter, wherein the internal junction is positioned between an aspiration tube and the lumen of the aspiration catheter.

20. An aspiration thrombectomy method for removal of a target occlusive material from a body passageway, comprising:
  engaging, by a scooped-out portion of a substantially spherical element of a cutting instrument of an aspiration thrombectomy system, the target occlusive material at a proximal point of the substantially spherical element, wherein the cutting instrument is associated with a distal end of an aspiration catheter of the aspiration thrombectomy system, wherein the cutting instrument comprises a spiral body connected to the substantially spherical element, wherein a distal point of the substantially spherical element is configured to be an atraumatic tip, and wherein the cutting instrument is configured for one or more motions comprising one or more of axial motion and rotational motion;
  providing, via an aspiration source, a negative pressure gradient to alter a level of pressure in the aspiration thrombectomy system to draw occlusive material into the aspiration catheter;
  providing or removing, via a plurality of valves in fluid communication with the aspiration thrombectomy system, fluids to alter a level of pressure in the aspiration thrombectomy system; and
  cutting and removing, by the aspiration thrombectomy system, the target occlusive material from the body passageway based on the one or more motions of the cutting instrument and changes to the level of pressure in the aspiration thrombectomy system.

* * * * *